(12) United States Patent
Hatano et al.

(10) Patent No.: US 9,182,359 B2
(45) Date of Patent: Nov. 10, 2015

(54) APPARATUS AND METHOD FOR INSPECTING PATTERN DEFECT

(75) Inventors: Hisashi Hatano, Hitachinaka (JP); Hiroyuki Yamashita, Hitachinaka (JP); Hidetoshi Nishiyama, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 485 days.

(21) Appl. No.: 13/386,243

(22) PCT Filed: Jun. 21, 2010

(86) PCT No.: PCT/JP2010/004106
§ 371 (c)(1),
(2), (4) Date: Feb. 2, 2012

(87) PCT Pub. No.: WO2011/010425
PCT Pub. Date: Jan. 27, 2011

(65) Prior Publication Data
US 2012/0268742 A1 Oct. 25, 2012

(30) Foreign Application Priority Data
Jul. 23, 2009 (JP) ................................. 2009-171719

(51) Int. Cl.
*G01N 21/95* (2006.01)
*G01N 21/956* (2006.01)
*G01R 31/265* (2006.01)
*H01L 21/68* (2006.01)

(52) U.S. Cl.
CPC .......... *G01N 21/956* (2013.01); *G01N 21/9501* (2013.01); *G01R 31/2656* (2013.01); *H01L 21/681* (2013.01)

(58) Field of Classification Search
None
See application file for complete search history.

(56) References Cited

U.S. PATENT DOCUMENTS

| | | | | |
|---|---|---|---|---|
| 4,567,525 A | * | 1/1986 | Endo et al. | 348/246 |
| 5,274,446 A | * | 12/1993 | Ashida | 348/192 |
| 7,835,015 B1 | * | 11/2010 | Wright et al. | 356/609 |
| 2004/0096125 A1 | * | 5/2004 | Alderson et al. | 382/312 |
| 2004/0145664 A1 | * | 7/2004 | Kobayashi et al. | 348/246 |
| 2006/0233434 A1 | * | 10/2006 | Hamamatsu et al. | 382/149 |
| 2008/0304064 A1 | * | 12/2008 | Kurosawa | 356/399 |
| 2009/0279079 A1 | * | 11/2009 | Shibata et al. | 356/237.3 |
| 2011/0055646 A1 | * | 3/2011 | Mukherjee et al. | 714/719 |

FOREIGN PATENT DOCUMENTS

| | | | |
|---|---|---|---|
| JP | 62-89336 A | | 4/1987 |
| JP | 1-117024 A | | 5/1989 |
| JP | 4-152545 A | | 5/1992 |
| JP | 5-218163 A | | 8/1993 |
| JP | 09214839 A | * | 8/1997 |
| JP | 11-271236 A | | 10/1999 |
| JP | 2001183301 A | * | 7/2001 |
| JP | 2004340647 A | * | 12/2004 |
| JP | 2005-17123 A | | 1/2005 |
| JP | 2007-64921 A | | 3/2007 |
| JP | 2009257903 A | * | 11/2009 |

OTHER PUBLICATIONS

Japanese Office Action received in Japanese Patent Application No. 2009-171719 mailed on Oct. 2, 2012.

\* cited by examiner

*Primary Examiner* — Gordon J Stock, Jr.
(74) *Attorney, Agent, or Firm* — Mattingly & Malur, PC

(57) ABSTRACT

Provided is a pattern defect inspecting apparatus wherein inspection performance is stabilized. The defect inspecting apparatus, which has a plurality of configuration units and inspects defects on the surface of a sample, is provided with a means for monitoring time-dependent changes and failures of some of or all of the configuration units, and a means for notifying the user of the results of the monitoring. Furthermore, a unit which can perform correction is provided with a correcting means, and also a means for replacing a failure component with a spare component which has been prepared in the device.

6 Claims, 14 Drawing Sheets

Alarm notification :
- The adjustment width of the X stage exceeds the deterioration threshold value.
    Replace the stage.

Malfunction notification :
- The adjustment width of the X stage exceeds the malfunction threshold value.
    Replace the stage.

Deterioration notification :
- Illumination light source is deteriorated.
    Inspect the illumination light source.

Normal

Abnormal

Normal

Abnormal

Top view

Side view

Top view

Side view

FIG.18A
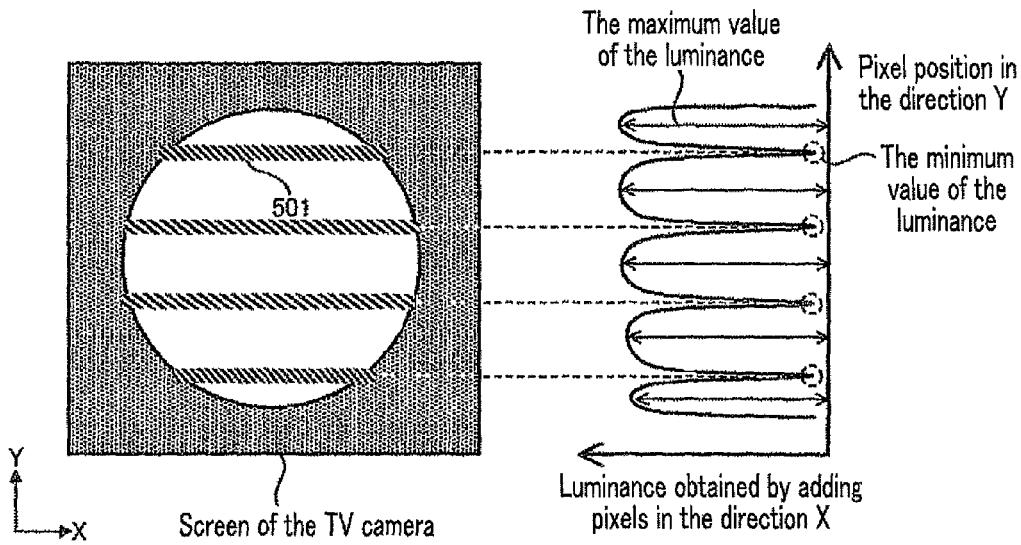
FIG.18B
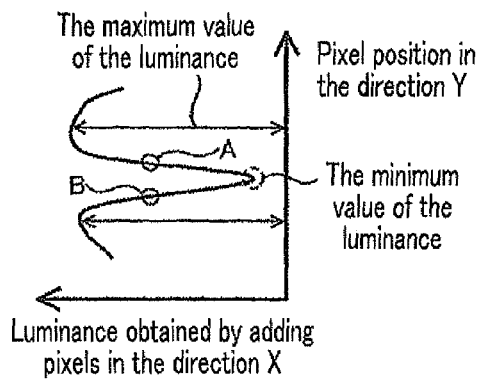
FIG.19A  FIG.19B  FIG.19C
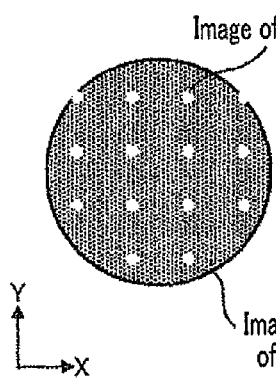 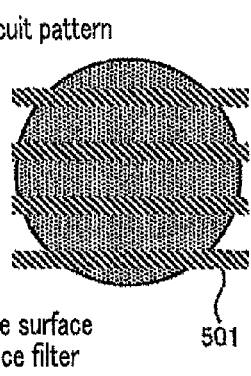 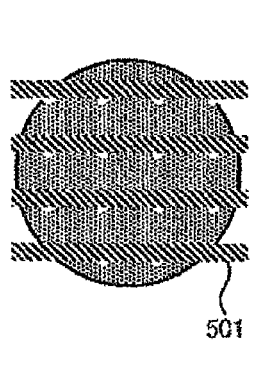

Top view

Side view

FIG.23A
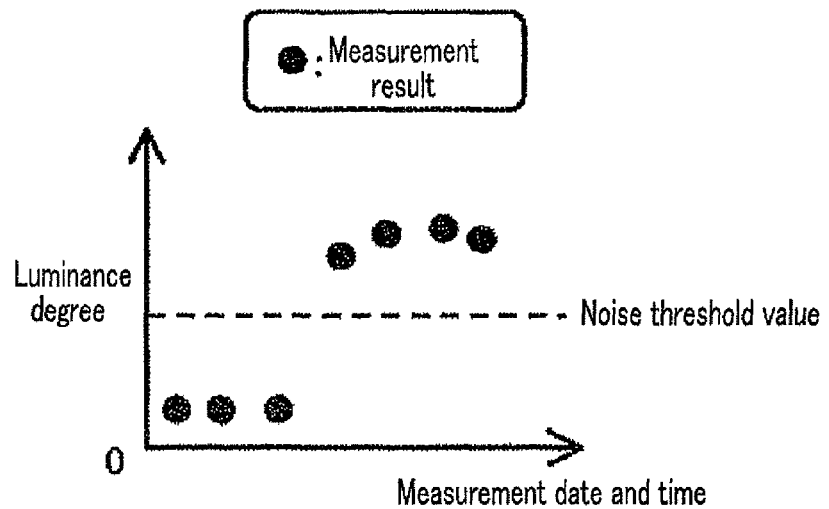
FIG.23B
Deterioration notification :
· Electric noise is increased. Inspection required.
FIG.23C
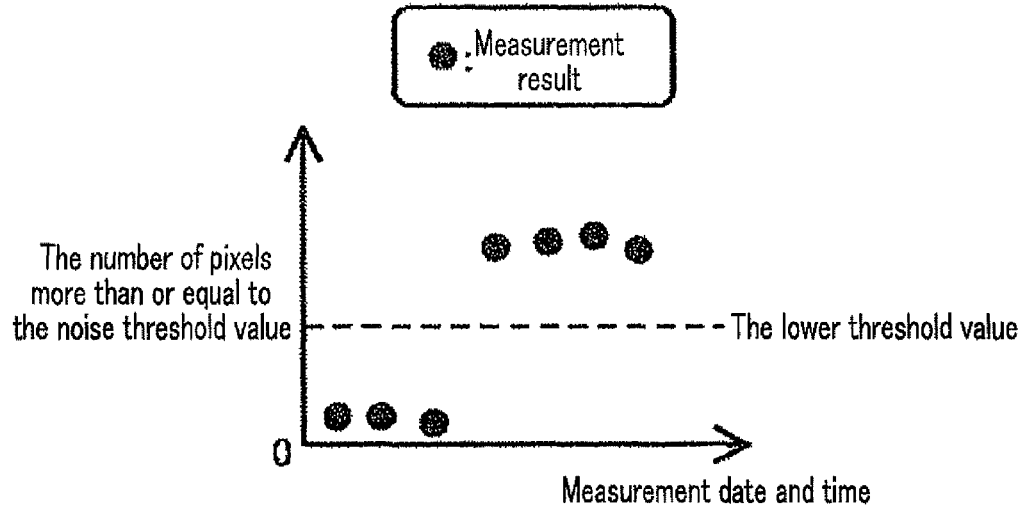

APPARATUS AND METHOD FOR INSPECTING PATTERN DEFECT

TECHNICAL FIELD

The present invention relates to a pattern defect inspecting apparatus which detects foreign substance or a defect on the circuit pattern of a sample. As a sample, a semiconductor wafer, a liquid crystal panel, a patterned media such as HDD, or a wafer for solar battery may be used. The present invention is described below by taking a semiconductor wafer as an example.

BACKGROUND ART

If there are a foreign substance or a defect (short-out or breaking of wire, etc.) on a semiconductor wafer in the semiconductor manufacturing process, the foreign substance or the defect may cause insulation failure or short circuit of a wiring or a capacitor, or the film failure of a gate oxide film, which may result in the failure of the semiconductor device.

In order to improve the yield of the semiconductor device, it is important to rapidly detect a foreign substance or a defect on the semiconductor wafer in a manufacturing process. A SEM (Scanning Electron Microscope) inspection technique or an optical inspection technique have been publicly known as a technique for detecting a foreign substance or a defect on the semiconductor wafer. The optical inspection technique includes a bright field inspection technique and a dark field inspection technique. In the bright field inspection technique, light is irradiated through an objective lens on the wafer and the reflected and diffracted light are collected through the objective lens. The collected light is photoelectrically converted by the detector so that a defect of the wafer is detected in signal processing. On the other hand, in the dark field inspection technique, light is irradiated on the wafer outside of the NA (Numerical Aperture) of an objective lens and the scattered light is collected by the objective lens. Similarly to the bright field inspection technique, the collected light is subjected to signal processing to detect a defect.

As an optical dark field inspection technique, a method is disclosed (in Patent document 1) in which a highly sensitive and highly reliable foreign substance inspection without false report by a pattern is realized by irradiating a laser on the wafer to detect the scattered light from the foreign substance and comparing the scattered light from the foreign substance with the inspection result of the same type wafer which has been inspected immediately before.

Further, as a technique for inspecting the foreign substance, a method is disclosed (in Patent documents 2 to 4) in which coherent light is irradiated on the wafer and light generated by the repeated patterns on the wafer is eliminated by the space filter to emphasize and detect a foreign substance and a defect which are not repeated.

PRIOR ART DOCUMENTS

Patent Documents

Patent document 1: Unexamined Japanese Patent Application Publication No. 62-89336
Patent document 2: Unexamined Japanese Patent Application Publication No. 01-117024
Patent document 3: Unexamined Japanese Patent Application Publication No. 04-152545
Patent document 4: Unexamined Japanese Patent Application Publication No. 05-218163

SUMMARY OF THE INVENTION

Problems to be Solved by the Invention

It is important to keep the detection sensitivity of the defect inspecting apparatus constant for highly sensitive yield control in the semiconductor device manufacturing. This is because there is a risk that a defect factor which should be detected normally is overlooked and the semiconductor devices are continued to be manufactured with the yield being low if an inspection device whose detection sensitivity gets lowered. As a factor of the change in the detection sensitivity, time degradation or malfunction of each unit (an illumination system, a delivery system, a detection system and processing system) of the defect inspecting apparatus is considered.

Furthermore, it has been desired to decrease the manufacturing cost of the semiconductor device as the price of the semiconductor device is decreased recently. Thus, it has been also desired to improve the operation rates of inspection devices so as to decrease the inspection cost. As a factor of the decrease in the operation rates, a case is considered where a defect inspecting apparatus gets malfunctioned one day without expectation, and it takes time to procure a part that replaces a malfunctioned part.

An object of the present invention is to realize a pattern defect inspecting apparatus and a pattern defect inspecting method whose performance is stable by keeping the detection sensitivity of the defect inspecting apparatus constant and making the malfunction time shorter.

Means to Solve the Problems

A characteristic of the present invention is to provide a defect inspecting apparatus which includes a plurality of configuration units and inspects a defect on the surface of a sample, wherein the defect inspecting apparatus includes a unit for monitoring time-dependent changes of some of or all of the configuration units and a means for notifying the user of the failure of each unit which has been monitored.

Another characteristic of the present invention is that, for a unit which can be corrected, the defect inspecting apparatus is provided with a unit for determining whether or not the unit which can be corrected is in a state where the unit is allowed to be corrected and a unit which corrects the unit.

A characteristic of the present invention other than those described above is that the defect inspecting apparatus is provided with a unit for replacing a failure component with a spare component which has been prepared in the apparatus.

The characteristics of the present invention described above and the other characteristics of the present invention other than those described above are described in detail below.

Effect of the Invention

According to an embodiment of the present invention, a pattern defect inspecting apparatus and a pattern defect inspecting method whose performance is stable can be realized by keeping the detection sensitivity of the pattern defect inspecting apparatus constant in accordance with the time-dependent change of each unit and making the malfunction time shorter.

BRIEF DESCRIPTION OF THE DRAWINGS

FIGS. 18A and 18B are illustrations showing a method for calculating the position of the shielding plate from an image.

FIGS. 19A to 19C are illustrations for describing another embodiment in which the position of the illustration shielding plate is calculated.

FIGS. 23A to 23C are illustrations for showing another example of the method for monitoring the detector.

EMBODIMENT FOR CARRYING OUT THE INVENTION

An embodiment of the present invention is described in detail below with reference to the accompanying drawings.

Figure 1:
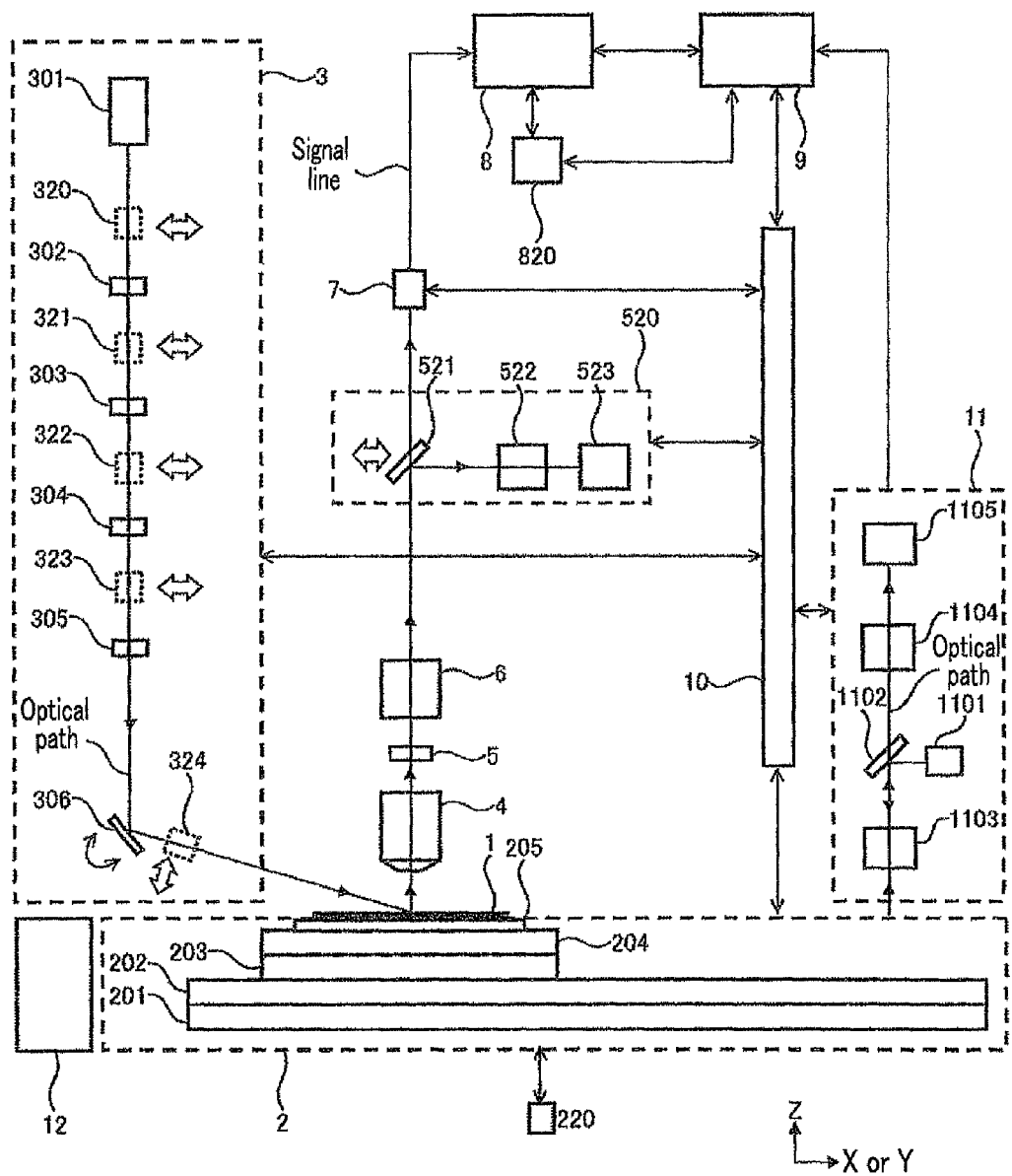
FIG. 1 is an illustration showing a schematic configuration of a pattern defect inspecting apparatus to which an embodiment of the present invention is applied.

FIG. 1 is a schematic configuration diagram of a pattern defect inspecting apparatus to which the embodiment of the present invention is applied. The present invention is described below by taking as an example the case where the present invention is applied to the inspection of a semiconductor.

A pattern defect inspecting apparatus shown in FIG. 1 includes a delivery system 2 on which a wafer 1, which is an inspection subject, is placed for moving the wafer 1, a status monitoring unit 220 for monitoring the status of the delivery system 2, a lighting unit 3, an objective lens 4, a space filter 5, an imaging lens 6, a status monitoring unit 520 for monitoring a lighting unit 3 or a space filter 5, a detector 7, a signal processing circuit 8, a status monitoring unit 820 for monitoring the status of the signal processing circuit 8; an input/output unit 9, a controller 10 for each unit, a wafer observation system 11, a wafer delivery system 12 and a relay lens or a mirror (not shown). It is to be noted that the arrows connecting the controller 10 to each unit (a part of the units is not shown) indicate that the controller 10 and the each unit send control signals, or the like to each other.

Each unit is described in detail below.

Firstly, the detail of the delivery system 2 is described. The delivery system 2 includes an X axis stage 201, a Y axis stage 202, a X axis stage 203, a θ axial stage 204, and a wafer chuck 205. The X axis stage 201 can be moved in a constant speed, and the Y axis stage can be step-moved. By using the X axis stage 201 and the Y axis stage 202, any position of the wafer 1 can be moved below the center of the objective lens 4.

Further, the X axis stage 203 has functions of lifting the wafer chuck 205 up and down and moving the wafer 1 to an object-side focus position of the objective lens 4 based on signals from an automatic focusing mechanism (not shown). Furthermore, the θ axial stage 204 has a function of rotating the wafer chuck 205 to match the advancing directions of the X axis stage 201 and the Y axis stage 202 with the rotation direction of the wafer 1. Further, the wafer chuck 205 has a function of fixing the wafer 1 by sucking the wafer 1 in a vacuum or the like.

The status monitoring unit 220 of the delivery system 2 can measure performance of the delivery system 2. An example of the status monitoring unit is described in detail below.

Figure 2:
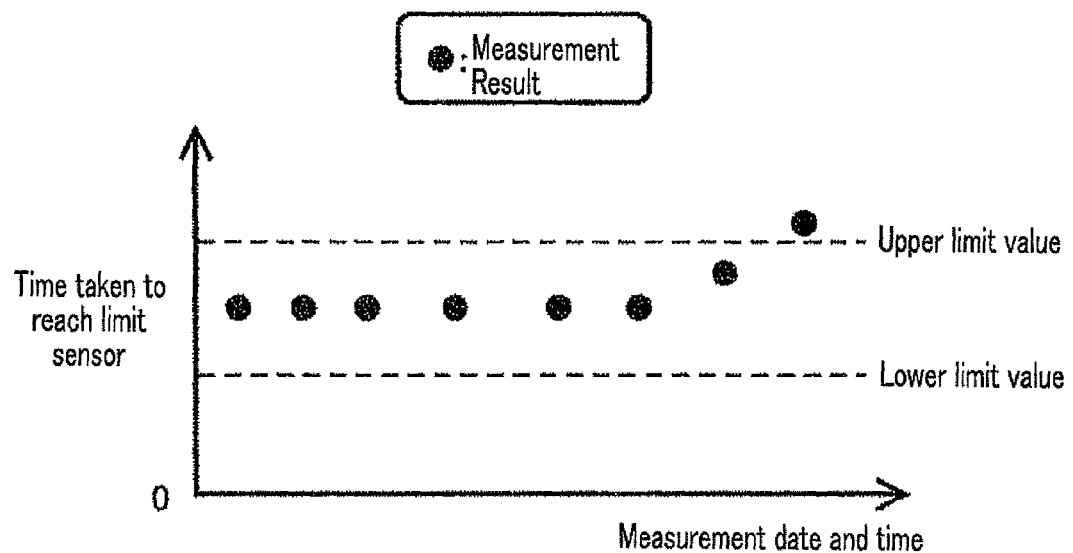
FIG. 2 is a graph for explaining a monitoring unit of a delivery system.

Firstly, a method for utilizing a limit sensor of the stages is described. The time taken for a stage to complete its movement from the time when the stage is commanded to be moved may be elongated due to the deterioration of a motor or the malfunction of a stage controller. Therefore, the deterioration or malfunction of the stage can be checked by monitoring the movement time of the stage. For example, since the position of the limit sensor of the stage is known in advance, it is only necessary to measure the time taken for the stage to move to the position of the limit sensor from an origin position. The measurement result is notified by the input/output unit 9 that the stage is deteriorated or malfunctioned if the measurement result exceeds maximum threshold value or minimum threshold value which are set for the time taken for the stage to move to the position of the limit sensor as shown in FIG. 2. Here, the maximum value and the minimum value may be determined based on values that are measured in advance or may be determined based on design values.

Further, if the control of the stage is performed in a closed loop, the stop position is finely adjusted based on information from a laser scale, however, the adjustment length may become larger because of the deterioration of the stage. For example, in the case where the adjustment length is 0.1 mm when the X axis stage 201 is moved 100 mm at one time, but the adjustment length becomes 1 mm when measured after some period of time, the stage may be deteriorated or malfunctioned.

Figure 3:
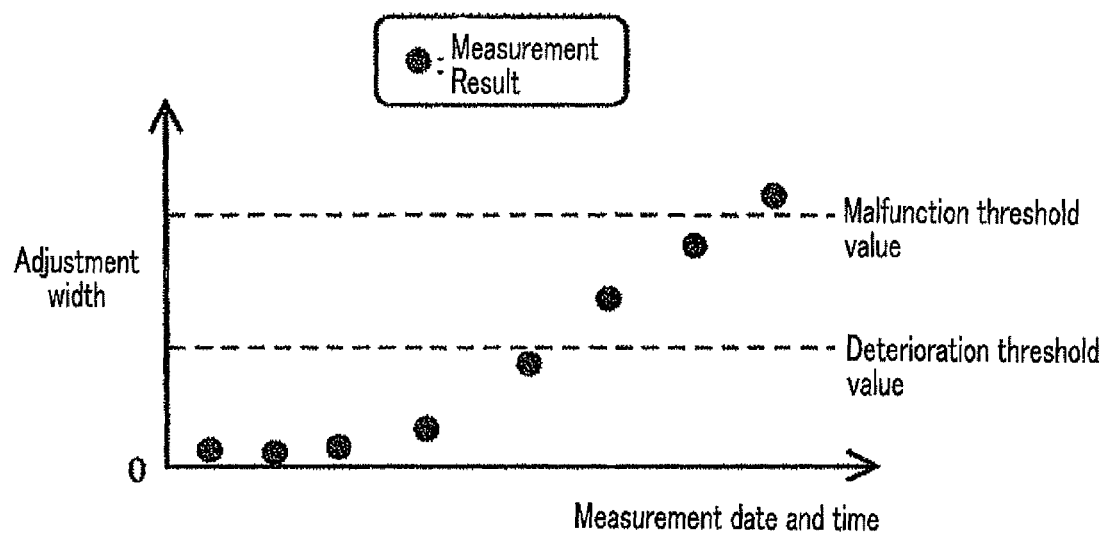
FIG. 3 is a graph for explaining another example of the monitoring unit of the delivery system.
Figures 4A, 4B, 5, 6:
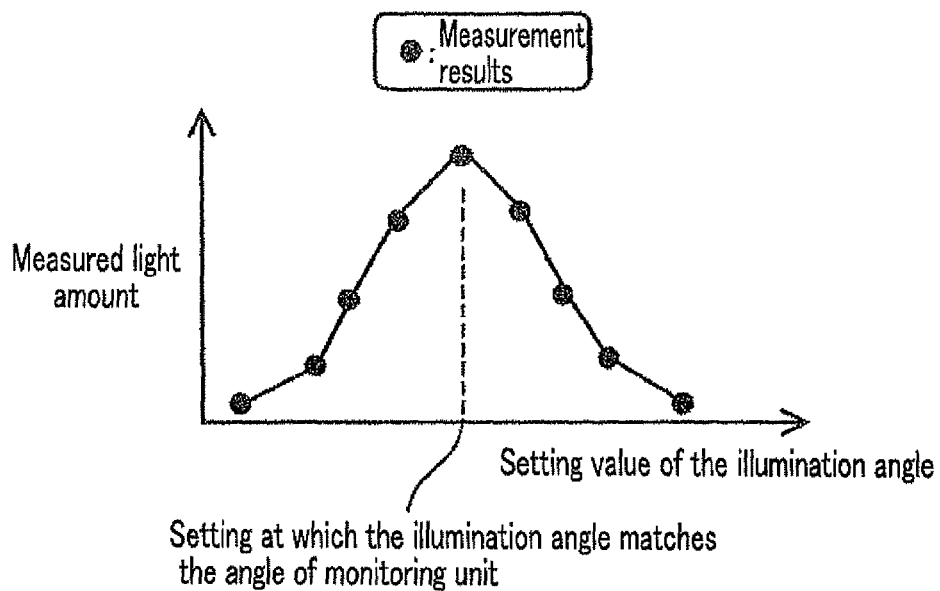
FIGS. 4A and 4B are illustrations describing screen displays of the delivery system.
FIG. 5 is an illustration describing a screen display when an illumination unit is deteriorated.
FIG. 6 is a graph showing a method for monitoring an illumination elevation angle.

Therefore, the status monitoring unit 220 of the delivery system 2 just has to plot information on the adjustment length as shown in FIG. 3 and determine and manage the deterioration threshold value or the malfunction threshold value. In FIG. 3, the lateral axis indicates a date and time when the status monitoring unit 220 obtains data, and the vertical axis indicates the adjustment length. The deterioration threshold value is a threshold value for notifying the deterioration of the stage. When the measured result exceeds the threshold value, the notification shown in FIG. 4A is displayed in the input/output unit 9. The malfunction threshold value is a threshold value for notifying the malfunction of the stage. When the measured result exceeds the malfunction threshold value, the notification shown in FIG. 4B is displayed in the input/output unit 9. It is to be noted that the deterioration and malfunction threshold values may be determined based on the specification of the stage.

It is described that the notification shown in FIGS. 4A and 4B are displayed in the example described above, however, the graphs shown in FIGS. 2 and 3 may be displayed to allow the user to check the condition of the stage in any time. Further, the X axis stage is described in the above example, however, similar configuration may be applied to the stages of the other axes.

Further, the variation of the speed or acceleration may be monitored because the speed or the acceleration can be calculated from the relationship of the positions and the times in the case where a measuring device such as the laser scale for measuring the position of the stage is provided to the stages of each axis. It may be configured that the possibility of the deterioration or the malfunction of the stages is notified if the speed and acceleration differ from those of the expected control movement by the amount of more than several percentage when the speed and acceleration are compared with those of the expected control movement.

Further, the static performance of the stage may be monitored. For example, when the X axis stage 201 is moved, if the Y axis stage 202 which should be stopped is not stopped (i.e. the scale of the Y axis stage is not constant), the Y stage may be deteriorated or malfunctioned.

In the embodiment, the delivery system of X axis movement and Y axis movement are described, however, the similar monitoring can be performed in a delivery system of other types such as R, θ movement (the type where a sample is scanned with linear movement and rotational movement).

Next, the lighting unit 3 has a function of shaping illumination light for irradiating the wafer 1, and includes an illumination light source 301, a light amount adjusting unit 302, a polarization direction adjusting unit 303, an illumination width adjusting unit 304, a condensing unit 305, and an elevation angle switching mirror 306. There is a plurality of the status monitoring units of the lighting unit 3 and each of the status monitoring units is indicated by the reference numerals 320 to 324 in FIG. 1. The lighting unit 3 is described in detail below.

The illumination light source 301 is a laser light source or a lamp light source. Since a laser light source can shape an illumination area which has the high brightness, the amount of light scattered from a defect can be made larger. Thus, the laser light source can be effective in high speed scanning. On the other hand, as the lamp light source has lower interference by light, there is an advantage that the effect for reducing speckle noise is excellent. It is to be noted that the range of the wave lengths of the laser light source may be visible lights, ultraviolet light, deep ultraviolet light, vacuum ultraviolet light and extreme ultraviolet light, etc. The oscillation form of laser may be a continuous oscillation or a pulsed oscillation. The wavelength is preferably equal to or less than approximately 550 nm. For example, the light source of 532 nm, 355 nm, 266 nm, 248 nm, 200 nm, 193 nm, 157 nm or 13 nm may be used.

As a laser light source, a laser which makes a solid state YAG laser (wavelength 1024 nm) be subjected to a wavelength conversion in a nonlinear optical crystal to generate the second harmonic (SHG), the third harmonic (THG) or the fourth harmonic (FHG) of the fundamental harmonic, an excimer laser or an ion laser may be used. A laser light source may be used which resonates two lights having different wavelength to oscillate a light having another wavelength. An example of this is a method for outputting a laser having wavelength 199 nm by resonating the sum of the SHG wave of an Ar laser light having wavelength of 488 nm and a YAG laser light having wavelength of 1064 nm.

Further, the type of the pulsed oscillation laser may be a low frequency pulsed oscillation laser whose oscillation frequency is several Hz or a quasi-continuous oscillation mode laser whose oscillation frequency is dozens to hundreds of Hz. Further, the method of pulsed oscillation may be a Q-switch type or a mode lock type. The advantages of each light source are described below.

Firstly, if a light source of short wavelength is used a resolution of an optical system is improved, and thus a highly sensitive inspection can be performed. Further, since the solid laser such as a YAG does not need an elaborate incidental equipment, the scale of the device can be made small and the cost thereof can be made lower. If the pulsed oscillation laser of high wavelength is used, a low cost optical part whose light transmittance and reflectance are low can also be used because the pulsed oscillation laser can be used in the same way as a continuous oscillation laser having high output power, and thus a low cost device can be realized. Further, as the coherent distance is short in a laser having a short pulse width, the laser having a short pulse has an advantage that reduction of the temporal interference can be made easy by adding a plurality of lights, each having different light lengths of illumination lights.

On the other hand a lamp light source may be used which emits light having the same wavelength range as that of the laser light source. As a lamp light source, an Xe lamp, an Hg—Xe lamp, an Hg lamp, a high pressure Hg lamp, a super high pressure Hg lamp or an Electron—Beam—Gas—Emission—Lamp (their output wavelength are 351 nm, 248 nm, 193 nm, 172 nm, 157 nm, 147 nm, 126 nm, 121 nm, for example) may be used as long as a desired wavelength can be output. When selecting a lamp, it is preferable to select a lamp whose output power of desired wavelength is high, and the arc length of the lamp is preferably short. This is because the formation of the illumination light becomes easy by using such a lamp.

Radiation amount of the light emitted from the illumination light source 301 is adjusted in the light amount adjusting unit 302. The adjustment of the light amount may be performed by using an attenuator which is comprised of ND (Neutral Density) filter, a ½ wavelength plate and a PBS (polarization beam splitter). The polarization direction of the light emitted from the light amount adjusting unit 302 is adjusted in the polarization direction adjusting unit 303. This adjustment is performed by using a ½ wavelength plate or a ¼ wavelength plate.

The illumination width of the light transmitted through the polarization direction adjusting unit 303 is adjusted by the illumination width adjusting unit 304. An example of the illumination width adjusting unit 304 is a beam expander.

This beam expander may have a fixed magnification or a plurality of magnifications. The beam expander with a fixed magnification has an advantage that the beam expander can be configured in a low cost. On the other hand, the beam expander with a plurality of magnifications has an advantage that when an illumination area is changed, it is possible to illuminate the area efficiently. As to a method for switching the magnifications, a plurality of beam expanders each having a fixed magnification may be changed or a mechanism having a plurality of magnifications by a zoom mechanism may be employed. The configuration in which a zoom mechanism is employed has an advantage that the configuration can be made smaller. The light transmitted through the illumination width adjusting unit 304 is collected by a converging optical system 305 and is irradiated on the wafer 1 by the elevation angle switching mirror 306.

The detail of the monitoring units 320 to 324 in the above described illumination system is described below. The monitoring units 320 to 324 are measurement equipment for measuring the illumination light amount, the polarization direction and the illumination width. The monitoring units 320 to 324 have mechanism by which the units can be placed on or removed from the optical path when the monitoring is required.

The monitoring unit 320 checks whether or not the light amount of the illumination light source 301 is output as designated. For example, if the illumination light source 301 is designed to output the output power of 1 W, 1 W should be measured by the monitoring unit 320. If the monitoring unit measures 0.8 W, however, there is a possibility that the illumination light source 301 is deteriorated or malfunctioned. In such a case, the input/output unit 9 outputs notification of deterioration or malfunction as shown in FIG. 5, and the illumination light source 301 is adjusted or replaced The monitoring unit 321 checks whether or not the light amount is adjusted by the light amount adjusting unit 302 as designed. The method for checking is to measure in advance the transmission rate of the light amount adjusting unit 302 and to compare the measured transmission rate with the data at the time of monitoring. If the transmission rate is lowered, it is preferable to replace the light amount adjusting unit 302. If the decrease in the transmission rate is due to the deterioration of the optical part, the position on which the illumination light is irradiated may be changed to use an area which is not deteriorated. To change the irradiation area, the light amount adjusting unit 302 is moved by a stage provided with a motor.

The monitoring unit 322 checks whether or not the polarization direction is adjusted as designed by the polarization direction adjusting unit 303. This check can be performed by obtaining in advance the setting of the polarization direction adjusting unit 303 and the data of the polarization direction and comparing the polarization direction measured by the monitoring unit 322 with the data of the polarization direction obtained in advance. If the measured polarization direction is different from the set polarization direction, the parameter of the polarization direction adjusting unit 303 is adjusted or the polarization direction adjusting unit 303 is replaced.

The monitoring unit 323 checks whether or not the illumination width adjusted by the illumination width adjusting unit 304 or the transmission rate are as designed. Therefore, the monitoring unit 323 preferably has a function of measuring a beam profile. When the illumination width is different from the set value, the illumination width adjusting unit 304 is adjusted or replaced. When the illumination width is too large for the measurement equipment used in the monitoring unit 323, a relay lens may be added to the monitoring unit 323 to narrow the illumination width. By making the illumination width narrower, the illumination width can be measured by a measurement equipment of which measurable beam radius is small, and thus the monitoring unit 323 can be comprised of a low cost measurement equipment.

The monitoring unit 324 can check the degradation degree of the converging optical system 305 and the elevation angle switching mirror 306. This check can be performed by comparing the illumination light amount measured in advance and the amount of illumination light from the converging optical system 305 and the elevation angle switching mirror 306. Alternatively, the ratio between the illumination light amount measured by the monitoring unit 323 and the illumination light amount measured in advance may be calculated to check the transmission rate and reflection rate. When the transmission rate or the reflection rate is not a desired value, the converging optical system 305 or the elevation angle switching mirror 306 are adjusted or replaced.

Further, it is possible to monitor the status of the elevation angle switching mechanism by measuring the light amount by the fixed monitoring unit 324 while the elevation angle switching mirror 306 is moved in an elevation angle, For example, when the illumination light amounts are plotted while the illumination elevation angle is changed, the result is as shown in FIG. 6. FIG. 6 shows that as the illumination elevation angle is deviated from a desired value, the illumination light is deviated from the measurement equipment of the monitoring unit 324 and the measured light amount is decreased. Thus, when the measured light amount does not become the maximum value at a desired illumination elevation angle, the illumination elevation angle may not be properly controlled. Therefore, the illumination light path or the elevation angle switching mirror 306 may need to be adjusted.

The objective lens 4 has a function of condensing light scattered from the area illuminated by the lighting unit 3. The aberrations of the objective lens 4 need to be corrected in a wavelength range of the illumination light. The type of the lens may be a refractive lens. When an illumination light source emitting light of the wavelength which does not transmit through the refractive lens is used, the type of the lens may be a reflective lens which is comprised of a reflective plate having a curvature.

The space filter 5 is used to optically remove information of the circuit pattern on the wafer 1. The Fourier transformation image of the pattern on the wafer 1 is formed by a pattern generated by condensing light on a position corresponding to the wavelength of the illumination light, the illumination angle and the repeated pitches of the pattern. By shielding the light condensing pattern by the space filter 5, it is possible to prevent the part of the light of the circuit pattern corresponding to the light condensing pattern from reaching the detector 7. As described above, as the light condensing pattern of Fourier transformation image is varied depending on the optical condition or the type of the circuit pattern, the space filter 5 needs to have a function of changing the shielding position.

Figure 7A:
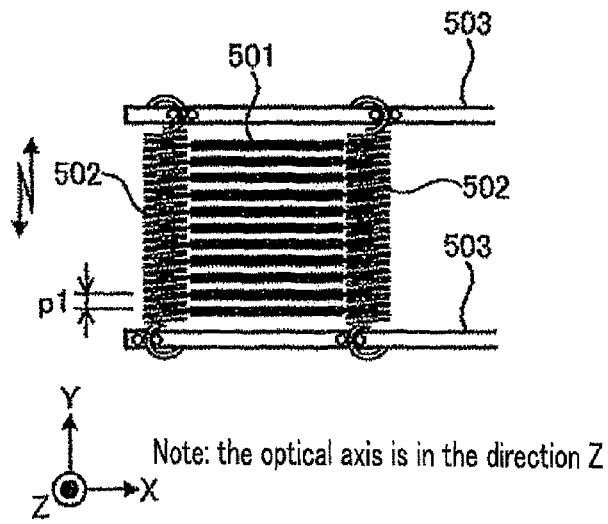
FIG. 7 is an illustration showing an example of a space filter.
Figure 7B:
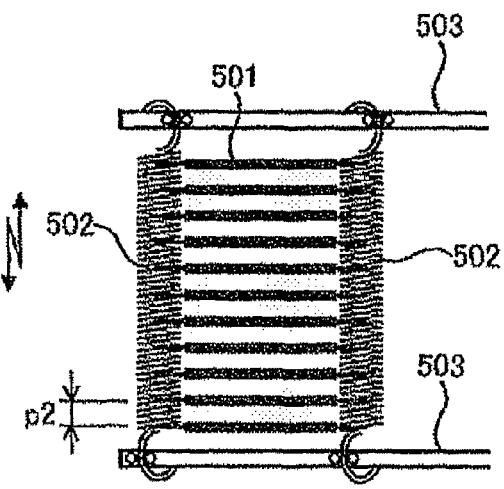

FIGS. 7A and 7B show an example of the space filter that can change the shielding position. FIGS. 7A and 7B are schematic views of the surface of the space filter which is perpendicular to the optical axis (the optical axis is in the Z direction). The space filter includes a plurality of shielding plates 501, two springs 502 and two supporting rods 503. The shielding plate 501 is for example a metallic plate, however, the shielding plate 501 may be any material without limited to a metallic plate as long as it has a light shielding function.

Both ends of the shielding plate 501 is connected to the spring 502 by solder or the like, and both ends of the spring 502 is fixed to the supporting rod 503. FIG. 7A shows the state of the space filter in which the pitch of the shielding plate 501 (the distance between the shielding plates) is set to be p1. In contrast, FIG. 7B shows the state of the space filter in which the supporting rod 503 is moved in the direction Y to extend the spring 502 and the pitch of the shielding plate 501 is changed to be p2. Thus, the pitch of the shielding plate can be adjusted by changing the interval between the supporting rods 503. Further, by moving the supporting rods 503 in the direction Y with the interval therebetween being kept, the light-shielding position can be moved in the Y direction.

The imaging lens 6 has a function of imaging a subject image of the wafer 1 on the detector 7. The imaging lens 6 is comprised of a plurality of single lenses for reducing optical aberration. Further, the imaging lens 6 has a function of moving each single lens or a group of the lenses.

The detector 7 has a function of photoelectrically converting incident light. An example of the detector 7 is an image sensor. The image sensor may be one dimensional CCD sensor or a TDI (Time Delay Integration) image sensor. A photomultiplier (photomultiplier tube) may be used. Moreover, a two dimensional CCD sensor such as a TV camera or a high sensitivity camera such as EB-CCD camera may be used. Further, a sensor may be used in which the detected pixels of the CCD are divided into a plurality of TAP to speed up. Further, a sensor provided with an anti-blooming function may be used. Further, a sensor of surface illumination type which irradiates light from the CCD surface or a sensor of rear surface illumination type which irradiates light from the surface opposite to the CCD surface. A sensor of rear surface illumination type is preferable for the wavelength which is shorter than the ultraviolet light.

When selecting a sensor which is used as the detector 7, a TV camera or a CCD linear sensor is preferable if the detector 7 is to be comprised of a low cost inspection device. A TDI image sensor, a photomultiplier or a EB-CCD camera is preferable if a sensor is desired to detect feeble light with high sensitivity. The advantage of the TDI image sensor is that the TDI image sensor can improve the SNR (Signal Noise Ratio) of the detected signals by adding the detected signals plural times.

When the TDI image sensor is used, the sensor is preferably driven in synchronization with the operation of the delivery system 2. Further, when a high speed operation is required, a sensor of TAP configuration is preferable. If the dynamic range of light received in the detector 7 is large (i.e. if light which is saturated for the sensor comes into the sensor) a sensor provided with an anti-blooming function is preferable.

Figure 8A:
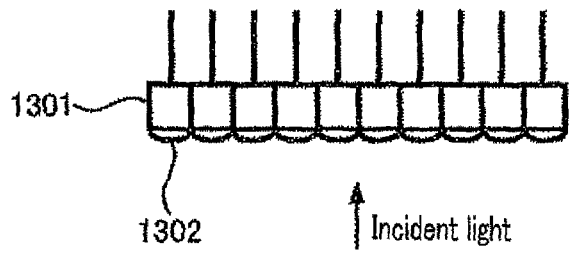
FIG. 8 is an illustration describing an example of a detector.
Figure 8B:
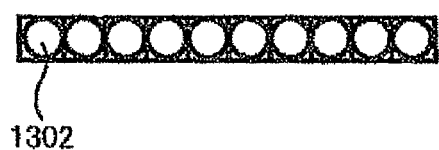
Figure 9:
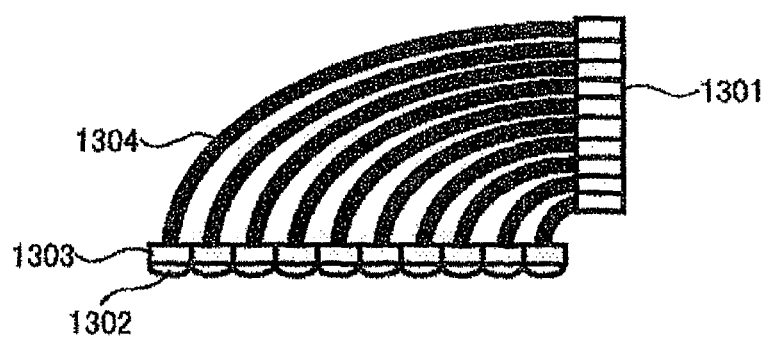
FIG. 9 is an illustration describing another example of the detector.

Next, a configuration example in which photomultipliers are used for the detector 7 is shown in FIGS. 8A, 8B and 9. FIG. 8A shows a side surface of the photomultiplier part. FIG. 8B shows the lower surface of the photomultiplier part. When the photomultiplier is used, the detector 7 can be used as one dimensional sensor with high sensitivity by arranging photomultipliers in one dimensional direction as shown in FIGS. 8A and 8B, and thus, the detector 7 can carry out a highly sensitive inspection. As a configuration of the above detector 7, the micro lens 1302 is attached to the side of the photomultiplier 1301 on which the incident light comes and the incident light is condensed into the photomultiplier 1301 by the micro lens 1302. The micro lens 1302 has a function of condensing light whose area is equal to or more than the photomultiplier surface into the photomultiplier 1301.

As another example, the detector 7 can be configured as shown in FIG. 9. Specifically, an optical fiber 1304 is attached to the micro lens 1302 via a holder 1303 arranged on the downstream side of the micro lens 1302, and the photomultiplier 1301 is attached to the output end of the optical fiber 1304. In this example, the sensor pitch can be made smaller than in the example shown in FIGS. 8A and 8B since the diameter of the optical fiber 1304 is smaller than that of the photomultiplier 1301, whereby a sensor having high resolution can be realized.

Figure 10:
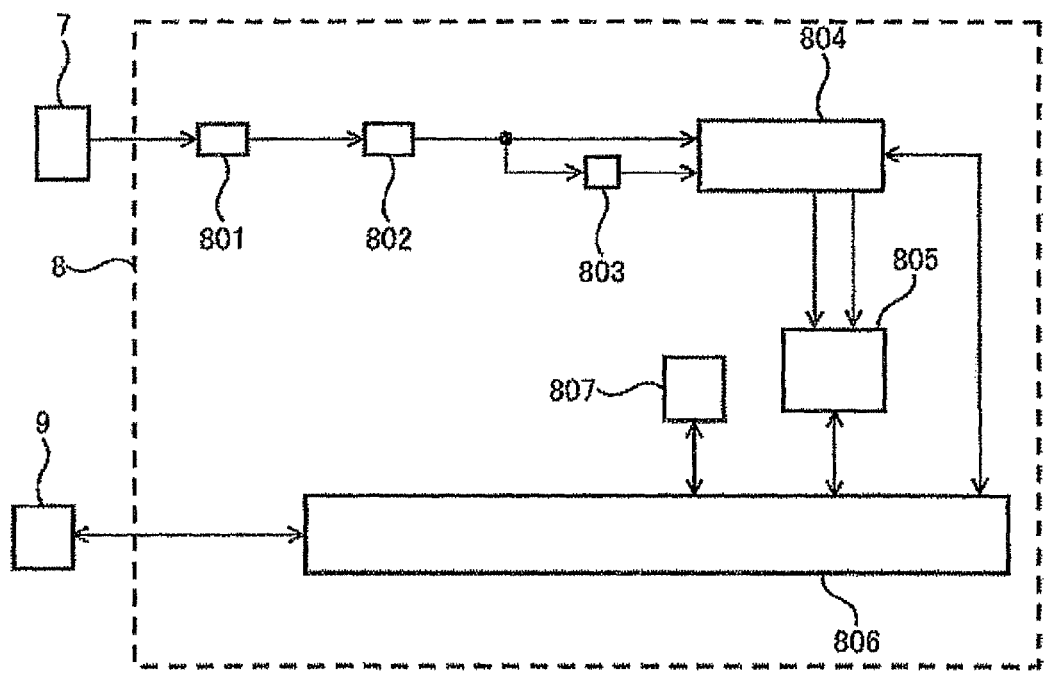
FIG. 10 is an illustration describing a detail of a signal processing unit.

Next, the signal processing circuit 8 is described in detail below with reference to FIG. 10. As shown in FIG. 10, the signal processing circuit 8 includes a gray-scale conversion unit 801, a filter 802, a delay memory 803, a position matching unit 804, a comparing processing unit 805, a CPU 806 and a storage 807.

The process of the signal processing circuit 8 is described below. Firstly, the gray-scale conversion unit 801 performs gray-scale conversion on the detection signal obtained by the detector 7. This gray-scale conversion is the conversion process as described, for example, in Unexamined Japanese Patent Application Publication No. 08-320294. The gray-scale conversion unit 801 corrects a signal by linear transformation, a logarithmic conversion, an exponential transform, a polynomial transform and the like.

Next, the filter 802 is a filter for eliminating an optical characteristic noise from the signal on which the gray-scale conversion has been performed by the gray-scale conversion unit 801. The filter is, for example, an averaging filter. The delay memory 803 is a signal storage unit for delaying the signal which is used in position matching process performed in a later stage and having a function of storing the signals output from the filter 802 in the amount of the repeated unit which constitutes the wafer 1 (i.e. one cell or a plurality of cells or 1 die or a plurality of dies). Here, a cell is a repeating unit of the circuit pattern in a die.

Next, the position matching unit 804 has a function of detecting the amount of the position displacement between the signal output from the filter 802 (a detection signal obtained from the wafer 1) and a delay signal (a reference signal which is used as a reference) obtained from the delay memory 803 by a normalized correlation method to perform position matching by the unit of pixel or a unit of equal to or less than a pixel.

The comparing processing unit 805 is a part which compares the detected signals output from the position matching unit 804 to detect a defect based on the difference in their characteristic amounts. By inputting the layout information of a device on the wafer 1 from the input/output unit 9, the CPU 806 creates defect position in the layout on the wafer 1 and characteristic amount data to store them in the storage 807. The defect position and the characteristic amount data are sent to the input/output unit 9 as appropriate. The detailed configuration of the comparing processing unit 805 may be the same as that described in Unexamined Japanese Patent Application Publication No. 61-212708. The comparing processing unit 805 includes, for example, a circuit for detecting the difference signal regarding the signals on which the position matching has been performed, a circuit which binarizes the difference signal to detect discrepancy, a characteristic amount extraction circuit which calculates an area, a length (a projection length) or coordinates from the binarized output. If only the defect position is needed as a detection result, the characteristic amount extraction circuit does not have to be necessarily provided. In that case, it is needless to say that the characteristic amount data does not have to be stored.

These signal processing may be performed by assigning each process to each circuit board. Otherwise, a plurality of processing may be assigned to one circuit plate in such a manner that the gray-scale conversion unit 801 and the filter 802 are performed in the same circuit plate, for example.

Further, in order to increase the processing speed, it is possible to divide the processing by the TAP unit of the detector 7 and to make the signal processing to be parallelized.

Next, the input/output unit 9 is described. The input/output unit 9 is an interface part with a user and is also a unit for inputting or outputting data or control information. As input information from a user, the layout information of the wafer 1, the name of the process, the conditions of the optical system mounted on the inspection device of the present invention. Output information to the user is, for example, inspection defect or the type or images of the defect or the like.

Next, the configuration of the wafer observation system 11 is described. The wafer observation system 11 includes an illumination system 1101, a half mirror 1102, an objective lens 1103, the imaging lens 1104 and the detector 1105.

The wafer observation system 11 is capable of obtaining the bright field image of the wafer 1 or the dark field image of the wafer 1. The method for obtaining the image is to reflect the light from the illumination system 1101 by the half mirror 1102 to the side of the objective lens 1103 so as to irradiate the light on the wafer 1 through the objective lens 1103. The light reflected or scattered by the wafer 1 is focused on the detector 1105 by the imaging lens 1104 through the objective lens 1103 and the half mirror 1102 to be formed as an image. It is preferable that a laser light source or a lamp light source is used as the illumination system 1101. Especially, it is preferable that the light source can emit light of wide range from the ultraviolet light to the visible light. Further, it is preferable that the objective lens 1103 is configured to be capable of switching its magnification by a revolver. Further, a light and dark field objective lens is preferable. Further, the detector 1105 may be a TV camera. The wafer 1 is moved under the wafer observation system 11 by the delivery system 2 to irradiate the light from the wafer observation system 11 on the wafer 1.

Figure 11:
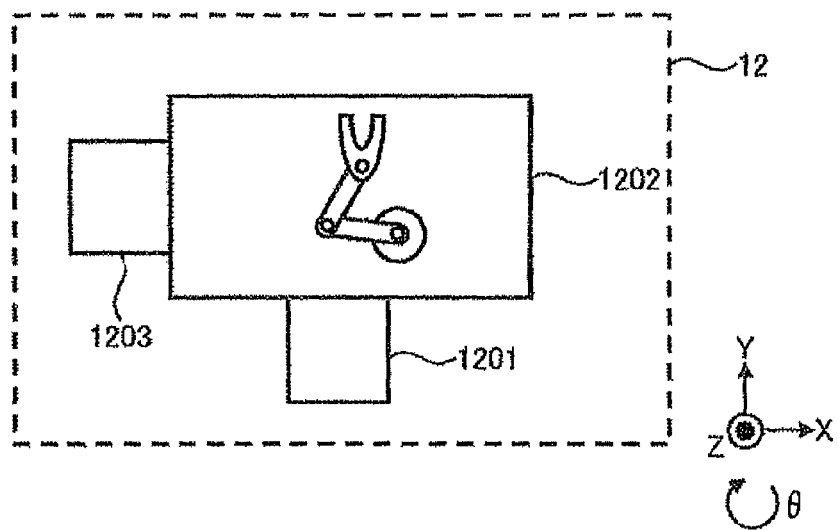
FIG. 11 is an illustration showing a detail of the wafer delivery system.

FIG. 11 is a schematic view of the wafer delivery system 12 for placing the wafer 1 on the delivery system 2. The wafer delivery system 12 includes a carrier opener 1201 which is provided with an apparatus which stores the wafer 1 (FOUP: Front Open Unified Pod, a wafer cassette or the like. Hereinafter, referred to as "FOUP"), a delivery unit 1202 which can take out the wafer 1 from the FOUP and move the wafer 1 in the directions of X, Y, Z and θ, and a pre-alignment device 1203 which adjusts the rotation direction θ and the position X, Y of the wafer 1 on a plane.

Next, the operations at the time of the inspection and the inspection preparation are described below.

Firstly, the operation for preparing the inspection of the wafer 1 is described. The wafer 1 is taken out from the FOUP provided to the carrier opener 1201, and is placed on the pre-alignment device 1203 by using the delivery unit 1202. The pre-alignment device 1203 roughly adjusts the rotation direction θ and the plane position X, Y of the wafer 1 in a predetermined position. After that, the delivery unit 1202 takes the wafer 1 from the pre-alignment device 1203 to place the wafer 1 on the delivery system 2 shown in FIG. 1.

The rotation direction θ of the wafer 1 placed on the delivery system 2 is finely adjusted by using the wafer observation system 11 and the delivery system 2.

In the fine adjustment operation, the wafer 1 is firstly moved to a position which is registered in advance. After that, an auto focusing mechanism (not shown) provided to the wafer observation system 11 moves the wafer 1 in a focus position of the objective lens 1103 to shoot an image, and calculates the position of the specific pattern registered in advance in the image. Next, the wafer 1 is moved to another die which is different from the die on which the specific pattern is imaged. The movement amount at this time is a distance which is obtained by multiplying the die pitch with the number of dies moved. After the wafer 1 is moved, the wafer 1 is imaged to calculate the position of the specific pattern in the image. The displacement of the wafer 1 in the rotation direction θ is calculated from the calculated position of the specific pattern in the image, and the θ axial stage 204 is finely adjusted to cancel the displacement.

After the θ axial stage 204 is finely adjusted, the wafer 1 is imaged again to calculate the position of the specific pattern in the image. Next, the wafer 1 is moved to another die and the position of the wafer 1 in the image of the specific pattern is calculated in the way similar to the above-mentioned method to calculate the displacement of the wafer 1 in the rotation direction. When the displacement of the wafer 1 in the rotation direction becomes small enough, the fine adjustment operation is finished.

Next, the wafer 1 is moved to an inspection start position which is set in advance. After that, the wafer 1 is moved to the inspected-body side focus position of the objective lens 4 based on a signal from the auto focusing mechanism (not shown). With the above operations, the preparation for inspecting the wafer 1 is completed.

In the above explanation, the case is described in which the wafer 1 is placed on the delivery system 2 after the rotation direction θ and the plane position X, Y of the wafer 1 are roughly adjusted by using the pre-alignment device, however, without using the pre-alignment device, the rough adjustment and the fine adjustment can be performed after the wafer 1 is directly placed on the delivery system 2. When the pre-alignment device is not used, the pre-alignment device mechanism is not necessary, and thus, a low cost configuration is possible.

Next, the operation at the time of the inspection is described below.

The illumination light emitted from the lighting unit 3 is irradiated on the wafer 1. The light scattered due to the circuit pattern on the wafer 1 or the defect of the wafer 1 is collected by the objective lens 4, and some of or all of the signals of the circuit pattern is eliminated by the space filter 5. The light which has passed the space filter 5 (mainly the scattered light due to the defect) is collected by the imaging lens 6 and is subjected to photoelectric conversion in the detector 7 to be converted into an image signal. The image signal is transmitted to the signal processing circuit 8 and is subjected to the defect detection processing as described above to detect the defect of the wafer 1. The detection result is sent to the input/output unit 9. By moving the wafer 1 by the delivery system 2 while performing the above operations, the entire surface of the wafer 1 is inspected and the detected result is output to the input/output unit 9. It is to be noted that the detected defect can be observed by the wafer observation system 11.

Figure 12:
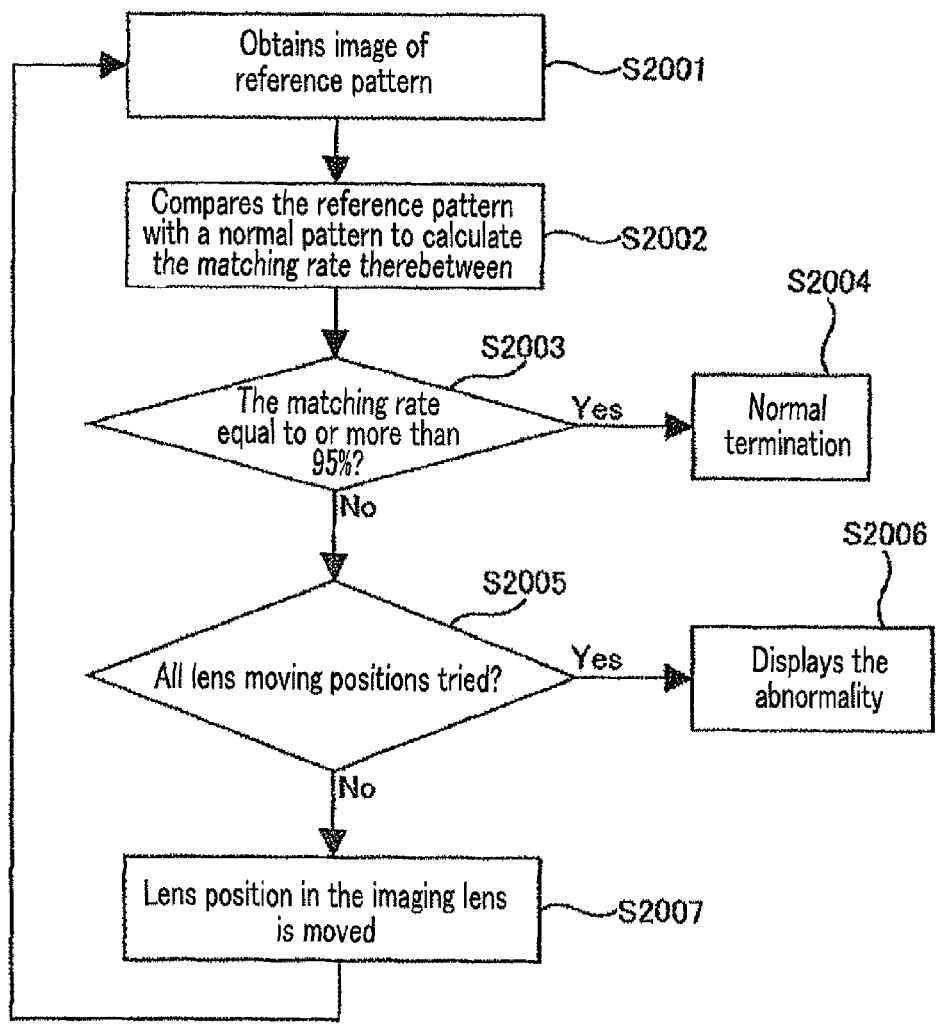
FIG. 12 is a flowchart showing a method for monitoring an imaging lens.

Next, the method for monitoring the imaging lens 6 is described. In order to evaluate the performance of the imaging lens 6, it is just necessary to check the image of a specific wafer or to check the detection luminance of the profile of a standard particle or a standard defect. The sequence of the monitoring is shown in FIG. 12. Firstly, a reference pattern of a specific wafer is imaged (S2001). Next, the reference pattern is compared with the image of the normal pattern which has been obtained in advance to calculate the matching rate of the images (S2002). The calculation of the matching rate is performed by a correlation pattern matching or the like. The matching rate is compared with a reference value (95% in the embodiment) (S2003), and if the matching rate is equal to or more than a reference value, the reference pattern is determined to be normal and the processing is terminated S2004).

On the other hand, if the matching rate is lower than the reference value, each lens or a group of lenses of the imaging lens 6 is moved (S2007) and an image is obtained again to calculate the matching rate. Then it is determined whether or not there is a new position to which the lens can be moved before the lens is moved (S2005). As the distance in which the lens can be moved is determined in advance, if the matching rate is not improved even when the lens is moved to all the positions, there is a possibility of degradation or malfunction, and thus, the possibility of the abnormality is notified to the input/output unit 9. When the abnormality is detected, the imaging lens 6 is replaced.

Figure 13A:
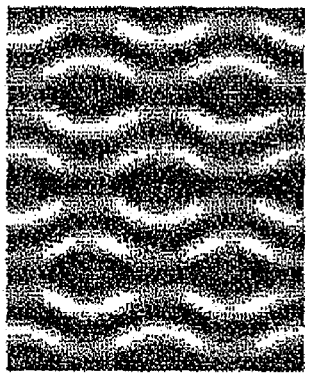
FIGS. 13A and 13B are illustrations for explaining a method for monitoring the imaging lens.
Figure 13B:

FIG. 13A shows an example image of a reference pattern when the reference pattern is normal. FIG. 13B shows an example image of the reference pattern having abnormality. As the aberration performance is decreased when there is an abnormality in the imaging lens 6, an obtained image will be a blurred image as shown in FIG. 13B. Thus, it is possible to determine the abnormality of the imaging lens 6 by comparing the images shown in FIGS. 13A and 13B.

Figure 14A:
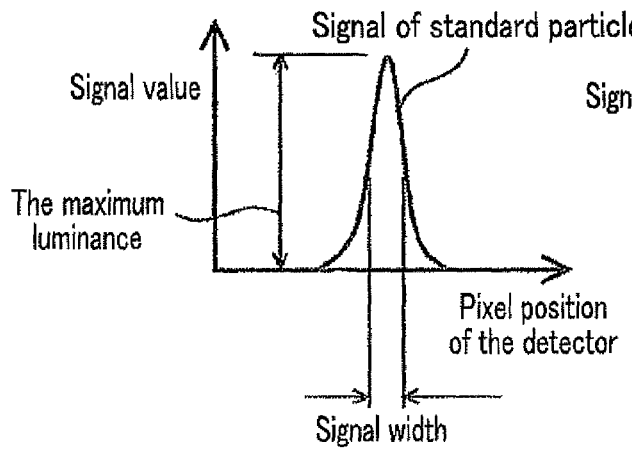
FIGS. 14A and 14B are illustrations for explaining another example of a method for monitoring the imaging lens.
Figure 14B:
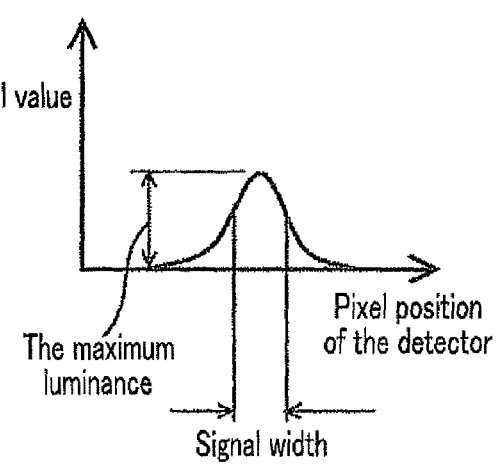

Further, in the above description, an image comparison with the reference image is used for explanation. However, a method may be used in which the characteristic amount (blurred degree, sharpness of an edge, etc.) of the image is calculated and the characteristic amount is compared with reference values. Alternatively, as described above, the detection luminance or the profile of the standard particle may be compared. When using a standard particle, it is just necessary to calculate the maximum luminance or the signal width from the signal waveform as shown in FIGS. 14A and 14B. The signal width may be obtained by calculating the distance between the positions of the luminance waveform which are half of the maximum luminance. As shown in FIGS. 14A and 14B in which the lateral axis represents the pixel location of the detector and the vertical axis represents the signal value, (B) the signal value of the maximum luminance of the signal of the standard particle at the time when the lens has abnormality is smaller than (A) the signal value of the maximum luminance of the standard particle at the time when the lens is normal. Further, the signal width of a signal of a standard particle at the time when the lens has abnormality is larger than the signal width of the signal of the standard particle when the lens is in a normal condition.

Figure 15A:
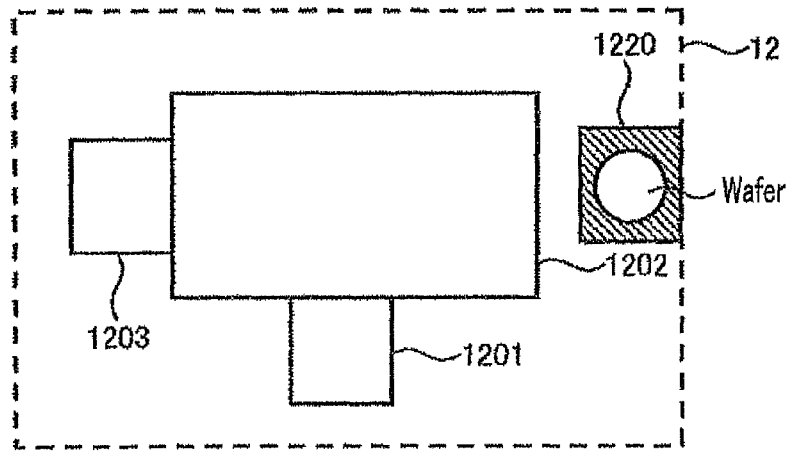
FIGS. 15A and 15B are illustrations for showing a method for arranging a monitoring wafer.
Figure 15B:
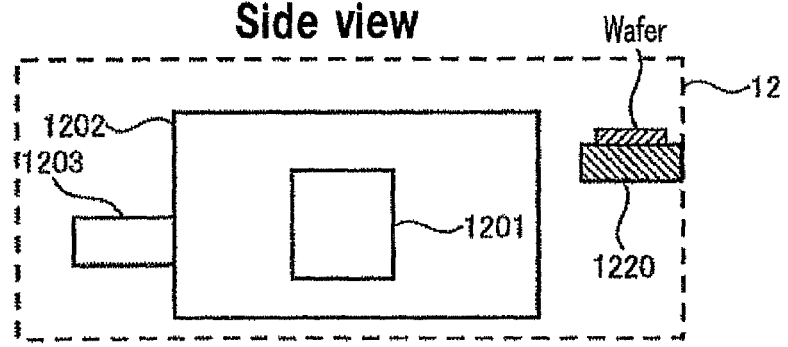
Figure 16A:
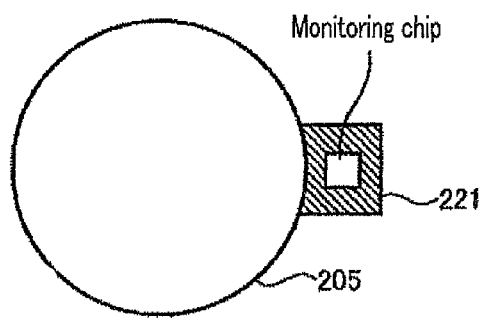
FIGS. 16A and 16B are illustrations for arranging a monitoring chip.
Figure 16B:
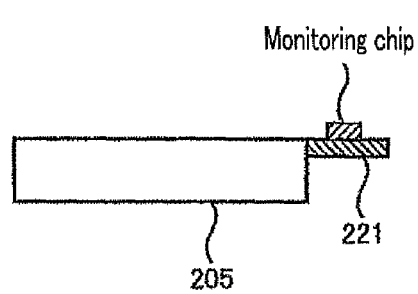

Further, the wafer used for the monitoring may be a wafer put in the FOUP or a wafer which is provided to the device of the present invention. When the wafer is provided to the device, it is just necessary to provide the monitoring wafer holding portion 1220 in a space of the wafer delivery system 12 as shown in FIGS. 15A and 15B. When the wafer put in the FOUP is used, there is an advantage that a plurality of wafers can be shared by a plurality of inspection devices to reduce the number of wafers used to reduce the cost. Further, in a case where the wafer is provided to the device, there is an advantage that monitoring can be performed without a human being or a high level system. If the cost for providing the wafer is to be reduced, a chuck 205 may be provided with a monitoring tip holder 221 for attaching a part of the monitoring wafer (a tip for monitoring) as shown in FIGS. 16A and 16B.

All the lenses do not necessarily have to be moved as described above, and it may be configured that only the lens which exerts the largest effect on aberration on the detection surface is moved. The deterioration check of a motor which moves each lens may be carried out by the stage check of the delivery system 2.

The status monitoring unit 520 for monitoring the lighting unit 3 or the space filter 5 is described in detail below. The status monitoring unit 520 includes an optical path switching mirror 521, a lens 522 which forms an image of the wafer 1 or the space filter 5, a detector 523 and a movement mechanism (not shown) which inserts or removes the status monitoring unit 520 into or from the optical path. The detector 522 is for example, a two dimensional camera.

Figure 17:
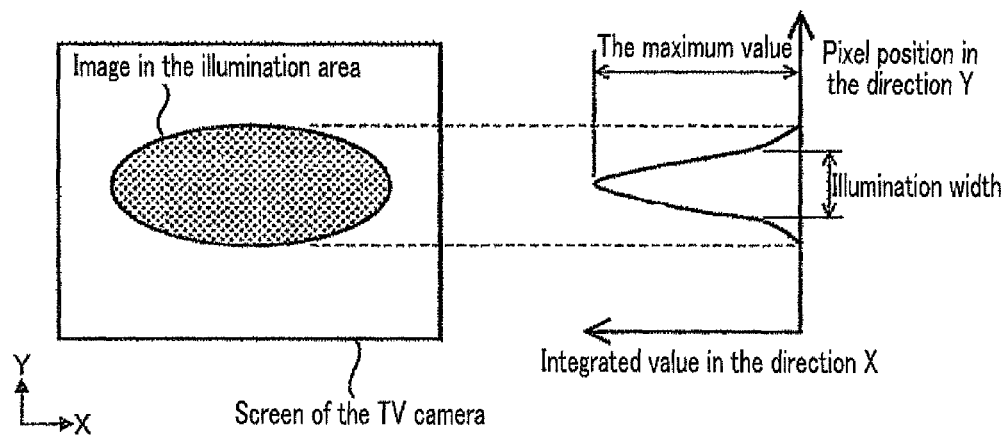
FIG. 17 is an illustration for explaining a method for monitoring an illumination unit.

A method for monitoring the status of the lighting unit 3 is described below. Firstly, a scattering object having concave and convex on its surface is placed on the focus position of the objective lens 4. Then the lighting unit 3 lights the scattering object, and the light scattered from the scattering object is reflected by the optical path switching mirror 521 through the objective lens 4 and the imaging lens 6 to form an image on the detector 523. From the image obtained in the detector 523, the illumination width or the illumination light amount of the lighting unit 3 is measured. The method for measuring the illumination width is described with reference to FIG. 17. FIG. 17 shows an image of illumination area obtained in the detector 523. The image of the illumination area in the screen of the TV camera is shown in the left side of FIG. 17. As shown in the right side of FIG. 17, when the illumination width in the direction Y is desired to be calculated, it is just necessary to integrate the luminance of the image in the X direction to calculate the illumination width from the integration data. The illumination width may be a width which is half of the maximum value of the integrated value or may be $1/(e^2)$. Further, as the illumination light amount, the maximum value of the integrated value may be used. The illumination width or the illumination light amount described above may be checked by comparing the illumination width or the illumination light amount with those measured in advance or design values. Further, a wafer or a ceramic plate on which a pattern is formed may be used for the above described scattering object as long as the wafer or ceramic plate have convex and concave on its surface.

Next, a method for monitoring the space filter 5 is described. The method is to check the pitch and position of the shielding plate 501 from the image of the space filter 5. Similarly to the case of the above-described lighting unit 3, firstly, the scattering object is placed, and the space filter 5 is provided at the predetermined motor pulse, and the image of the space filter 5 is obtained by the detector 523.

FIGS. 18A and 18B are an illustration of a TV camera screen showing an obtained space filter image and illustrations for explaining a calculation method for calculating the position of the shielding plate 501 in the image. Firstly, as shown in FIG. 18A, pixel addition is performed in the direction X in a space filter image, and the added luminance values are plotted in the direction Y. The reason why the pixel addition is performed in the direction X is to reduce the error due to the fluctuation of the luminance value of each pixel of an obtained image. The luminance maximum values and the luminance minimum value are obtained from the graph in which the added luminance values are plotted, and 2 points (A and B in FIG. 18B) which are pixels whose values are half of the luminance maximum value and the luminance minimum value are calculated, and the two half points are used as positions of the shielding plate 501. Similarly, the position of each shielding plate 501 is calculated, and distances between each shielding plate are calculated as a pitch. By checking whether or not the calculated pitch or the position is substantially the same as the predetermined values, the degradation or malfunction of the space filter 5 can be monitored.

Next a method for calculating the set position of the shielding plate 501 from the fourier transform image of the circuit pattern is described. Firstly, the lighting unit 3 lights a specific circuit pattern of a wafer determined in advance. The light scattered from the specific circuit pattern forms a fourier transform image which corresponds to the illumination wavelength, the illumination angle, the illumination direction and the repeated pitch of the circuit pattern. As shown in FIG. 19A, the image of the light condensing pattern (the fourier transform image) can be obtained in the detector 523 if the space filter is not set. On the other hand, if the fourier transform image is shielded by the shielding plate 501 the image obtained by the detector 523 will be as shown in FIG. 19B. When the shielding plate 501 is slightly displaced in the direction Y, the image obtained by the detector 523 will be as shown in FIG. 19C. More specifically, when the shielding plate 501 is placed in an appropriate position as shown in FIG. 19B, the fourier transform image becomes dark, and as the shielding plate 501 is displaced from an appropriate position as shown in FIG. 19C, the fourier transform image becomes brighter. Therefore, the luminance of each pixel of the fourier transform image is added to obtain an evaluation value, and the setting in which the evaluation value becomes the smallest is determined to be the position in which the shielding plate 501 is appropriately set.

Figure 20:
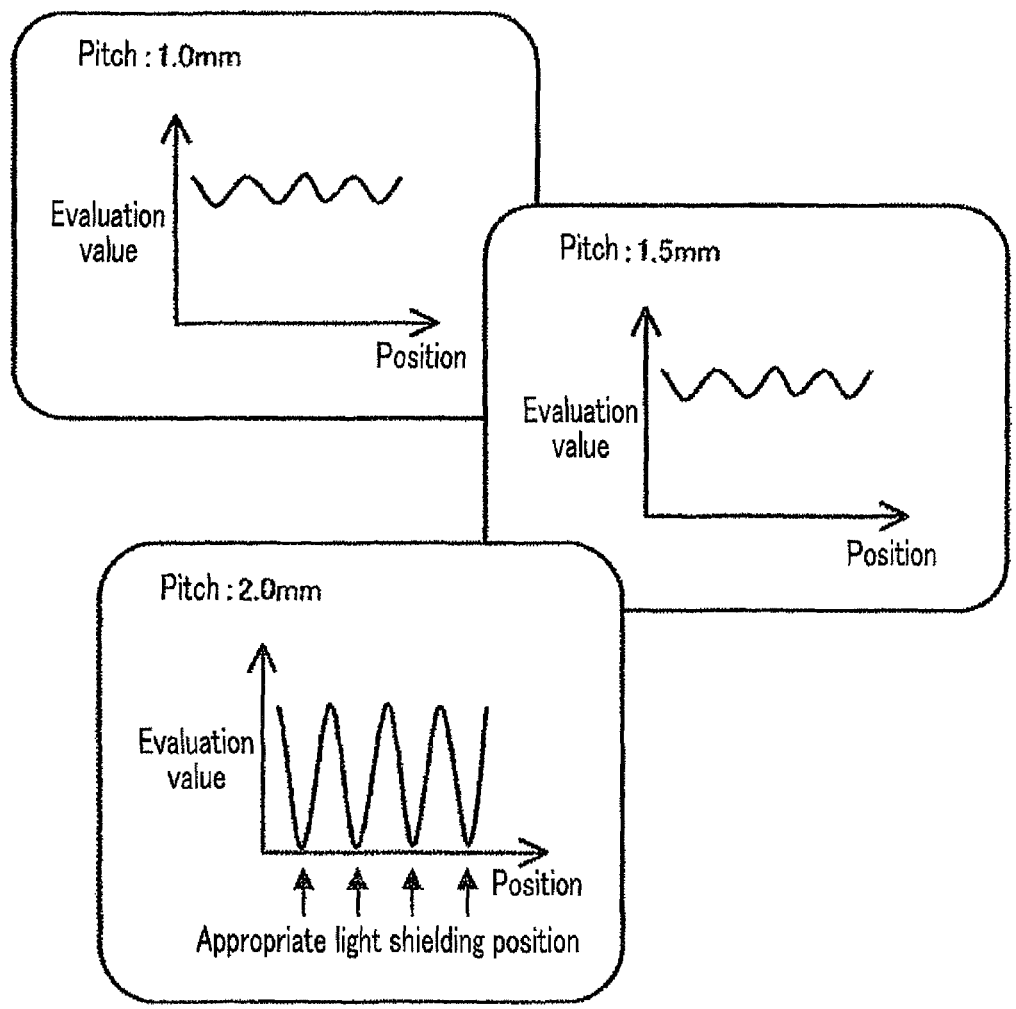
FIG. 20 is an illustration showing a screen display when calculating the position of the shielding plate.

FIG. 20 shows a display example at the time of evaluation. Graphs are made with two parameters of a pitch and a position of the shielding plate as shown in FIG. 20 since it is necessary to set the pitch and the position of the shielding plate 501 for setting the shielding plate 501. When setting the pitch and the position, it is just necessary to determine the graph having the smallest evaluation value in all the graphs as an appropriate pitch and position of the shielding plate 501 as shown, for example, in the graph provided in the lowest part in FIG. 20. It is to be noted that if the pitch of the fourier transform image is known in advance, data may be obtained just by moving the parameter of the position of the shielding plate 501.

In the embodiment, it is assumed that the fourier transform image is not changed in time. However, as the fourier transform image is varied due to the change in the illumination wavelength, the illumination angle and the illumination direction, it is preferable to check the illumination wavelength, the illumination angle and the illumination direction before monitoring the space filter 5. Further, an automatic calculation method is described in the embodiment, however, a set value may be obtained by setting the shielding plate 501 by a user. The method shown in FIG. 18 has an advantage that the method does not need a specific wafer. On the other hand, the method described here has an advantage that a scattering object is not needed.

Figure 21A:
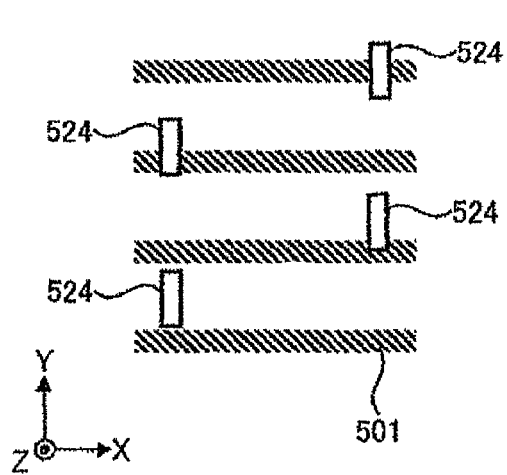
FIGS. 21A and 21B are illustrations for explaining a method for confirming the position of the shielding plate.
Figure 21B:
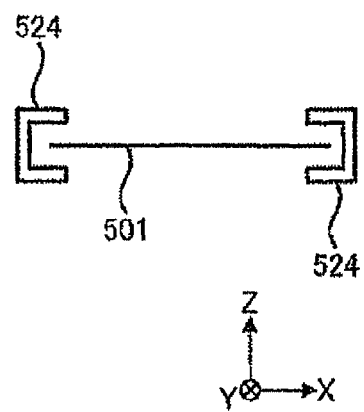

Another example for checking the position of the shielding plate 501 is described below with reference to FIG. 21. The example is a method for checking existence or non-existence of the shielding plate 501 by providing a photo sensor 524 at the position where the shielding plate 501 is placed when the shielding plate 501 is moved to a predetermined set value. More specifically, if all the photo sensors detect the shielding plate 501 when the shielding plate 501 is moved to the set value, it is determined that the shielding plate 501 is positioned normally. If any one of the photo sensors does not detect the shielding plate 501 when the shielding plate 501 is moved to the set value, it is determined that the shielding plate 501 is not placed appropriately. The determination result is displayed on a screen. This method has an advantage that the monitoring can be performed only by the space filter 5 without using a wafer or a scattering object.

Even if the position of the shielding plate 501 calculated by the method described above is different from a measured value obtained in advance or a design value, the space filter 5 may be used by correcting the set value of the pitch and the position of the shielding plate 501 when the pitch and the position have repetitive reproducibility and the difference is within a certain range. The method for measuring the repetitive reproducibility is to move the shielding plate 501 to set values of more than or equal to 2 pitches and positions and repeatedly move the shielding plate 501 to the set values of more than or equal to the 2 pitches about ten times, for example, and to check whether or not the shielding plate 501 is moved to the same pitch and the same position.

Figure 22:
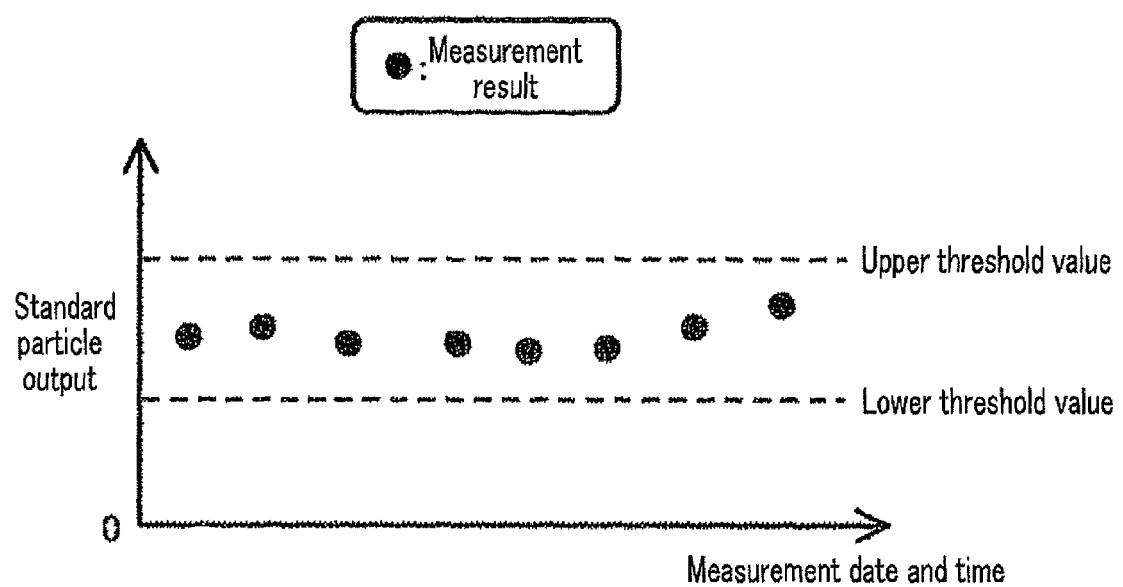
FIG. 22 is a graph for explaining a method for monitoring the detector.

The status monitoring unit of the detector 7 is described in detail below. In the monitoring of the detector 7, it is preferable to check the status of the photoelectric conversion efficiency and the electric noise. Now, the method for monitoring the photoelectric conversion efficiency is explained. Firstly, a wafer with standard particle is provided and light of a predetermined amount is irradiated on the wafer. At this time, the photoelectric conversion efficiency can be monitored by measuring the output power of the standard particle obtained by the detector 7. The screen display example is shown in FIG. 22. FIG. 22 shows a temporal variation of the output of the standard particle, and if the output of the standard particle exceeds an allowable range (the range between the upper threshold value and the lower threshold value in FIG. 22), an alarm is displayed.

Next, the method for monitoring the electric noise is explained. The electric noise can be monitored by measuring the luminance value which is output from each pixel of the detector 7 or calculating the number of pixels in which their luminance exceeds a predetermined value (noise threshold value) when light does not come into the detector 7. A display example of the monitoring is shown in FIGS. 23A to 23C. FIG. 23A shows the temporal development of the luminance of each pixel. If the luminance of the pixel exceeds the noise threshold value, an alarm message is displayed as shown in FIG. 23B. Further, FIG. 23C also shows the temporal development of the number of pixels of which luminance exceed the noise threshold value. Also in this case, an alarm is displayed as shown in FIG. 23B when the number of pixels of which luminance exceed the noise threshold value exceeds a lower threshold value.

Figure 24:
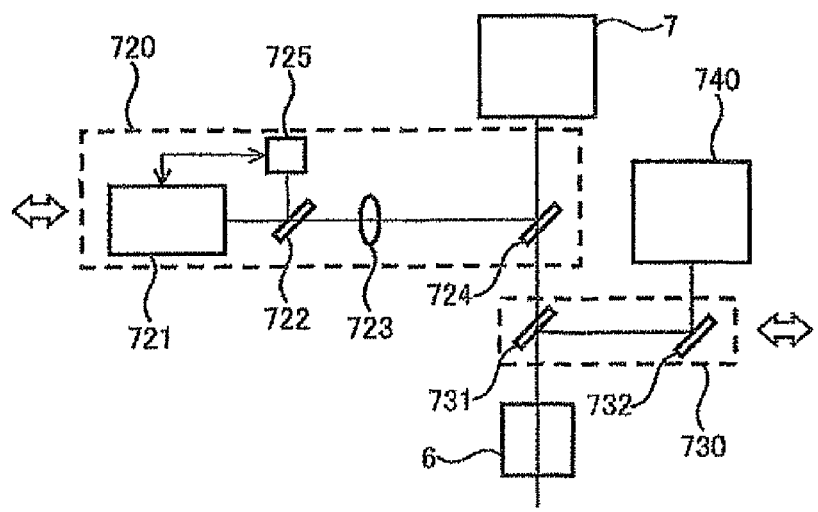
FIG. 24 is an illustration for explaining another example of the method for monitoring the detector.

Another example of the status monitoring unit of the detector 7 and a method for coping with the deterioration of the detector 7 are described with reference to FIG. 24. A device shown in FIG. 24 includes a light irradiation unit 720, a light path switching unit 730 and a backup detector 740. Further, the light irradiation unit 720 includes a standard light output unit 721, a beam splitter 722, a beam expander 723, a mirror 724, a light amount measuring device 725 and a unit (not shown) for moving the mirror 724.

The example described above is the example in which the output power of the standard particle is measured, however, the example described here is a method in which light is directly irradiated on the detector 7 and a photoelectric conversion efficiency is calculated based on the output value from the detector 7. In the example described here, firstly, the amount of the light emitted from the standard light output unit 721 is measured by the light amount measuring device 725 and the standard light output unit 721 is controlled to adjust the light amount to be a predetermined light amount. The light whose amount has been adjusted transmits through the beam splitter 722 and is expanded by the beam expander 723 to the size corresponding to the visual field of the detector 7. The light is reflected by the mirror 724 to be irradiated on the detector 7. The detector 7 monitors the deterioration of the photoelectric conversion efficiency by obtaining the luminance of each pixel and comparing the obtained luminance with a predetermined luminance. If the obtained luminance is lower than the predetermined luminance, for example, by equal to more than 10%, an alarm is output that the detector 7 is deteriorated.

If there is not enough time to replace the detector 7 although the detector 7 is deteriorated, the back up detector 740 is used. When the backup detector 740 is used, the light path switching unit 730 comprised of the mirrors 731, 732 switches the image forming optical path of the imaging lens 6 from the detector 7 to the backup detector 740. Here, it is necessary to arrange the detector 7 and the backup detector 740 in such a manner that the distance between the imaging lens 6 and the detector 7 and the distance between the imaging lens 6 and the backup detector 740 are equal. Since the device can be used continuously only by switching the optical path as described above, it is possible to shorten the time in which the device is stopped.

Next, the status monitoring unit 820 for monitoring the signal processing circuit 8 is described in detail. The status monitoring unit 820 for monitoring the signal processing circuit 8 is a substrate in which test data for performing an operation test on the signal processing circuit 8 is stored. A method for monitoring is performed in such a manner that the test data is input to the signal processing circuit 8 from the status monitoring unit 820 of the signal processing circuit 8 and the signal value processed in the signal processing circuit 8 is compared with a signal value which is expected as the processing result. If the signal values are the same, it is determined that the signal processing circuit 8 is normal. If the signal values are not the same, it is determined that the signal processing circuit 8 has some defect. This method includes a method for checking all the signal processing algorism (referred to as a full check) and a method for checking only a signal processing algorism which is used normally (referred to as an normal check). Since all the algorism is checked in the full check, the possibility of the defect can be made lower, but the processing takes a long time in the full check. On the other hand, in the normal check, the time taken for monitoring can be shortened, however, only a part of the algorisms is checked. Thus, it is preferable to use the full check and the normal check in combination. It is possible to efficiently monitor the signal processing circuit 8 by performing the normal check once a day and the full check once every month, for example. As to a temporary storage such as a memory element or the like, the temporary storage can be monitored by checking the read or write operation of the memory. If a defect of the signal processing circuit 8 is detected as a result of monitoring, a notification of the defect is output to the input/output unit 9 and the signal processing circuit board having defect is replaced.

The above described monitoring may not be necessarily performed on all the signal processing circuit board. For example, the monitoring time can be shortened by monitoring only a board which has high malfunction rate. The status monitoring unit 820 of the signal processing circuit 8 may be provided to each signal processing circuit board or a plurality of signal processing circuit boards may be checked by one monitoring unit. There is an advantage that each monitoring unit can be designed smaller by providing the monitoring units to every signal processing circuits. On the other hand, the configuration in which the monitoring unit is shared has an advantage that the cost of the device can be made lower.

Figure 25A:
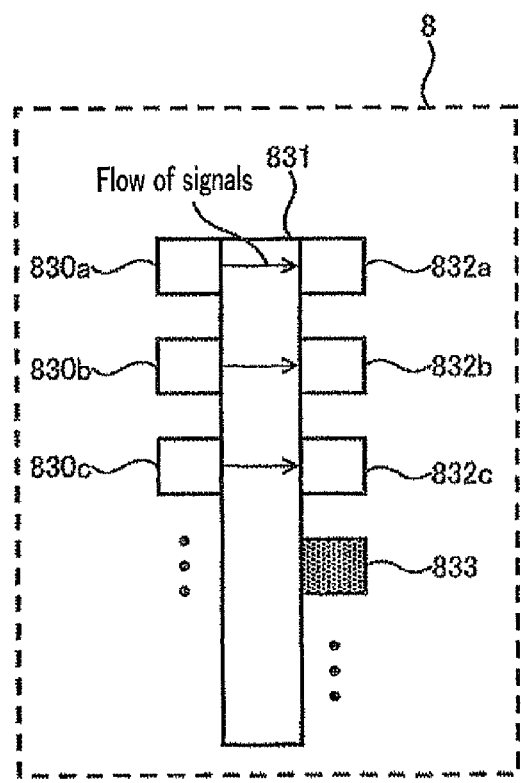
FIGS. 25A and 25B are illustrations for explaining an operation when the signal processing unit has a defect.
Figure 25B:
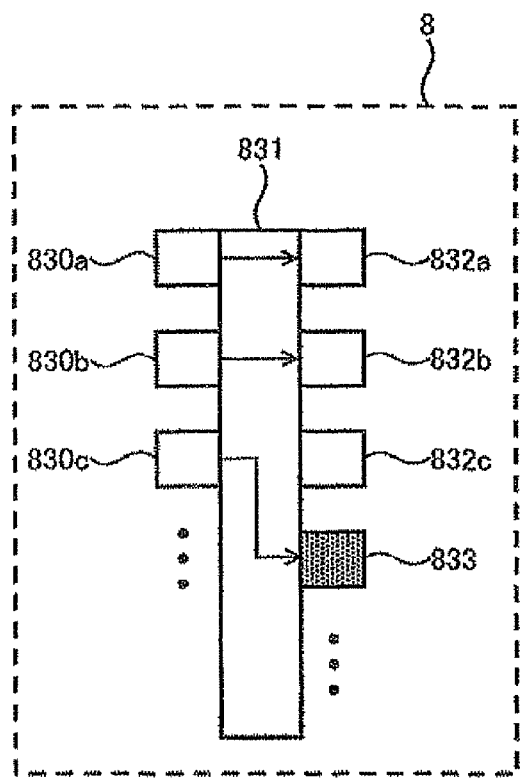

Next, a method for shortening a down time of the device when a part of the signal processing circuit 8 is malfunctioned is described with reference to FIGS. 25A and 25B. The method described below is a method in which a signal switching unit is added to the process. The device shown in FIGS. 25A and 25B is comprised of signal processing circuits 830a to 830c on the front side of the device, a signal switching unit 831, signal processing circuits 832a to 832c on the rear side of the device, and a backup circuit 833 for the signal processing circuits on the rear side of the device. If the signal processing circuit is normal, the signal processing circuits 830a, 830b, 830c are connected to the signal processing circuits 832a, 832b, 832c, respectively as shown in FIG. 25A. When a defect is found in the signal processing circuit 832c for example, a signal path is switched by the signal switching unit 831 to connect the signal processing circuit 830c on the front part to the backup circuit 833 so as to allow the signal processing circuit to perform an normal operation.

It is to be noted that each signal processing board may include a mechanism which allows to replace a processing circuit board having a defect without stopping the device. This makes it possible to shorten the time for replacing a board with a defect.

Figure 26:
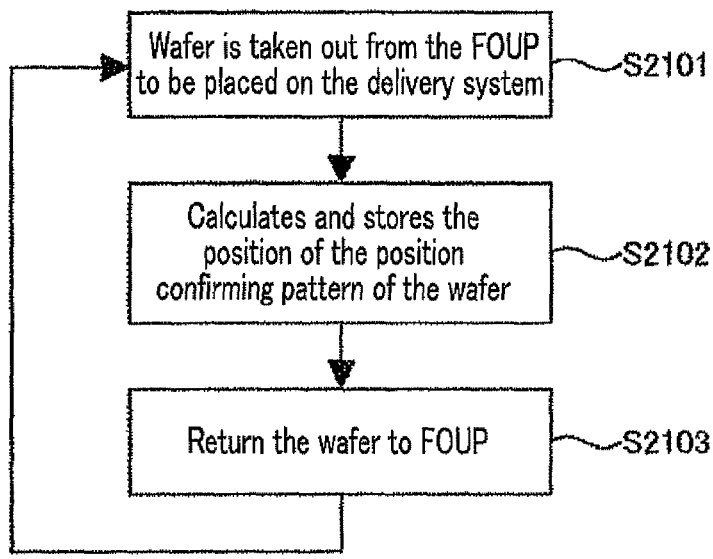
FIG. 26 is a flowchart for explaining the monitoring unit of the wafer delivery system.

A method for monitoring the wafer delivery system 12 is described below. An example method for monitoring the position reproducibility of the delivery unit 1202 is described with reference to FIG. 26. Firstly, a FOUP storing a wafer used for monitoring is provided to the carrier opener 1201. The wafer used for monitoring is placed on the delivery system 2 by the delivery unit 1202 (S2101). After the wafer is placed, the position confirming pattern on the wafer used for monitoring is recognized by the input/output unit 9 by using the delivery system 2 and the wafer observation system 11. The position of the recognized pattern is stored in the input/output unit 9 (S2102). The wafer used for monitoring is taken out from the delivery system 2 and is stored in the FOUP (S2103). The above operation is repeated plural times to calculate the position reproducibility range of the delivery unit 1202 based on the position of the pattern stored in each operation. Then the calculated position reproducibility range is compared with a position reproducibility range obtained in advance or a design value to check whether or not the range is changed. If the position reproducibility range is changed as a result of the check, it is determined that the delivery unit 1202 may be deteriorated or malfunctioned and the input/output unit 9 is notified of the deterioration of malfunction so that the delivery unit 1202 is adjusted or replaced.

Next, a method for monitoring the reproducibility of the position and the rotational angle of the pre-alignment device is described. Firstly, the FOUP which stores the wafer used for monitoring is provided to the carrier opener 1201. The wafer used for monitoring is taken out from the carrier opener 1201 by using the delivery unit 1202 and is placed on the pre-alignment device 1203. Then, the rotation direction θ and the positions X, Y on the plane of the wafer used for monitoring are adjusted by the pre-alignment device 1203. After that, the wafer used for monitoring is placed on the delivery system 2 from the pre-alignment device 173 by using the delivery unit 1202. By using the delivery system 2 and the wafer observation system 11, plural patterns for position confirming patterns at plural positions on the wafer used for monitoring are recognized. Based on the recognition result, the rotation direction θ of the wafer used for monitoring and the positions X and Y of the plane of the position confirming pattern is described. Then the calculated value is recorded in the input/output unit 9. The delivery unit 1202 takes out the wafer used for monitoring from the delivery system 2, places the wafer on the pre-alignment device 1203, and adjusts the rotation direction θ and the positions X, Y of the wafer used for monitoring on the plane. After that, the wafer used for monitoring is taken from the pre-alignment device 1203 by using the delivery unit 1202, places the wafer on the delivery system 2, calculates the rotation direction θ of the wafer used for monitoring and the positions X, Y of the position confirming patterns on the plane, and stores them in the input/output unit 9. The above described operations are repeated plural times, and the reproduction range of the values of the rotation direction θ and the positions X, Y on the plane is calculated based on the rotation direction θ and the positions X, Y of the plane stored in each operation. Then the reproduction range of the calculated values is compared with the reproduction range of values obtained in advance to check whether or not there is a change in the reproduction range. If there is a change in the reproduction range as a result of the check, the input/output unit 9 is notified of deterioration or malfunction of the pre-alignment device 1203 and the pre-alignment device 1203 is adjusted or replaced. It is to be noted that the reproduction range calculated by the present method includes the reproducibility of the delivery unit 1202. Therefore, it is necessary to check whether or not the delivery unit 1202 is normally operated by a method such as those described above before the present method is applied.

Figure 27A:
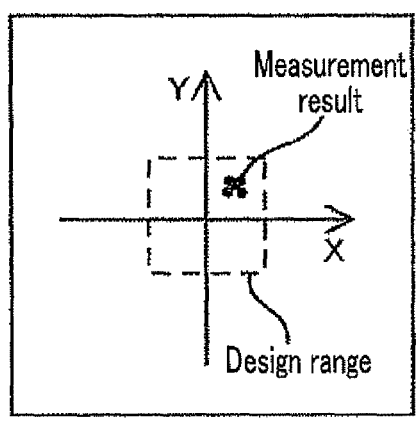
FIGS. 27A and 27B are graphs for explaining screen displays of the wafer delivery system.
Figure 27B:
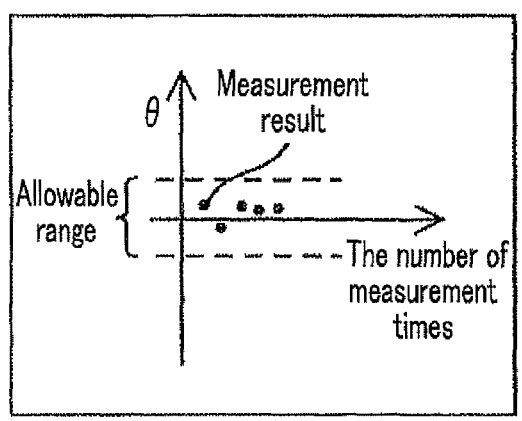

FIGS. 27A and 27B show a display example of the monitoring result of the wafer delivery system 12. FIG. 27A is an example showing measuring results of the positions X, Y of the plane. In this example, five measuring results are shown, however, more points may be plotted and past measuring results may be also plotted. An advantage of plotting past measuring results is that it is possible to check the temporal change of measuring results. A design range is shown by dashed lines in FIG. 27A. If the measuring result exceeds the design range, degradation or malfunction of the wafer delivery system 12 is notified by screen display.

Further, FIG. 27B shows an example of measuring results of the rotation direction θ. In this example, the number of measuring times is set in a lateral axis, and further, an allowable range is shown instead of the design range.

Figure 28:
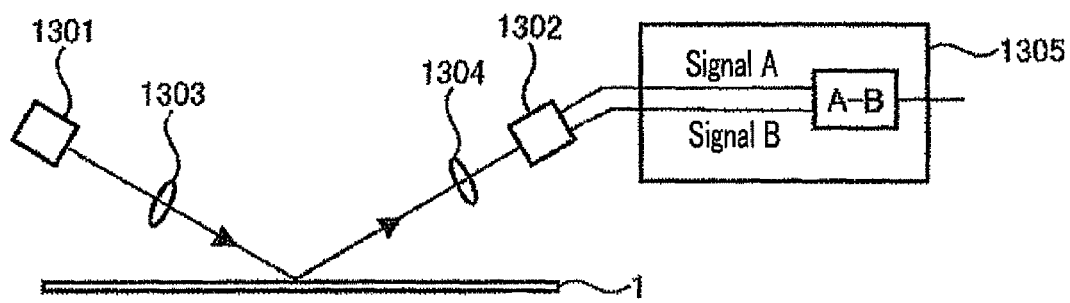
FIG. 28 is an illustration for explaining an auto focusing mechanism.

Next, an auto focusing (hereinafter, referred to as AF) mechanism which has not been shown above is described. The AF mechanism includes an illumination 1301 for auto focusing, a position sensor 1302, lenses 1303, 1304, and an electric circuit 1305, for example, as shown in FIG. 28. The AF mechanism beam-forms the illumination 1301 for auto-focusing by the lens 1303 to irradiate the light on the wafer 1, converges the light reflected from the wafer 1 by the lens 1304 to receive the light by the position sensor 1302, and determines that a position at which the difference signal of the output of the sensor 1302 is 0 is the focus position. The AF mechanism performs the operation described above to search for the focus position while moving the X axis stage 203 up and down.

Next, a method for monitoring the auto focusing mechanism is described. Firstly, the wafer used for monitoring is provided to the delivery system 2 and is moved to the vicinity of the inspected-body side focus position of the objective lens 4. At this position, the AF operation is repeated plural times to calculate the reproduction range of the position of the X axis stage 203. The calculated reproduction range is compared with a reproduction range obtained in advance or a design value to check whether or not there is a change in the reproduction change. In the embodiment described above, the method using the wafer used for monitoring has been described, however, a sample for monitoring (see FIG. 16) provided to the delivery system 2 may be used instead of the wafer used for monitoring.

All of the monitoring units which have been described above is not necessarily performed. Depending on the easiness of deterioration, the frequency of defect, the cost for configuring a monitoring unit, units to be monitored or monitoring units may be limited.

Further, a unit which manages monitoring of all the units may be provided. By providing the unit which manages to monitor all the units, the easiness of deterioration or the frequency of defect of each unit can be compared. Thus, it is possible to optimize the monitoring frequency or managing value of each unit. Further, it is obvious that operations described in each example may be applied to other examples.

As described above, in order to achieve an object that a pattern defect inspecting apparatus whose inspection performance is stable is realized, the specification discloses the pattern defect inspecting apparatus including a unit for monitoring the temporal change or malfunction of each unit and a unit for notifying a user of the result of the monitoring. The specification also discloses a unit that can perform correction is provided with a unit which executes correction. The specification also discloses a unit which replaces a part having a defect with a backup part prepared in the device in advance.

DESCRIPTION OF THE REFERENCE NUMERALS

1 Wafer
2 Delivery system
3 Illumination unit
4 Objective lens
5 Space filter
6 Imaging lens
7 Detector
8 Signal processing circuit
9 Input/output unit
10 Controller
11 Wafer observation system
12 Wafer delivery system
220 Monitoring unit of delivery system 2
520 Status monitoring unit of lighting unit 3 or space filter 5
820 Status monitoring unit of signal processing circuit 8

The invention claimed is:

1. A defect inspection apparatus to inspect for a defect on a surface of a sample, the defect inspection apparatus comprising:
   a plurality of configuration units including a detector and a light irradiation system to output a standard light;
   a status monitoring system to monitor a time dependent change of the performance of the detector by comparing a luminance of the standard light that the detector detects with a predetermined luminance; and
   a notification system to receive and display a result of the status monitoring system for each of the plurality of configuration units and including a system to process a signal output from the detector.

2. The defect inspection apparatus according to claim 1, further including;
   an observation system which acquires at least one of dark field image and a bright field image; and
   an illumination system for the observation system.

3. A defect inspection apparatus to inspect for a defect on a surface of a sample, the defect inspection apparatus comprising:
   a plurality of configuration units including a signal processing circuit;
   a status monitoring unit to monitor a time dependent change of the performance of the signal processing circuit wherein the status monitoring unit for monitoring the signal processing circuit is a substrate in which test data for performing an operation test on the signal processing circuit is stored; and a notification system to receive and display a result of the status monitoring unit for each of the plurality of configuration units.

4. The defect inspection apparatus according to claim 3, further including;
an observation system which acquires at least one of dark field image and a bright field image; and
an illumination system for the observation system.

5. The defect inspection apparatus according to claim 3, further comprising a signal switching system for switching a signal path to a normal signal processing circuit from a malfunctioning signal processing circuit.

6. The defect inspection apparatus according to claim 5, further comprising a system for replacing the malfunctioning signal processing circuit without stopping an electric supply to the signal processing circuit.

* * * * *